(12) United States Patent
Orlow et al.

(10) Patent No.: US 8,772,252 B2
(45) Date of Patent: *Jul. 8, 2014

(54) COUMARIN COMPOUNDS AS MELANOGENESIS MODIFIERS AND USES THEREOF

(75) Inventors: Seth J. Orlow, New York, NY (US); Li Ni Komatsu, Clarksville, MD (US)

(73) Assignee: New York University, New York, NY (US)

(*) Notice: Subject to any disclaimer, the term of this patent is extended or adjusted under 35 U.S.C. 154(b) by 12 days.

This patent is subject to a terminal disclaimer.

(21) Appl. No.: 13/360,619

(22) Filed: Jan. 27, 2012

(65) Prior Publication Data

US 2012/0220545 A1 Aug. 30, 2012

Related U.S. Application Data

(60) Provisional application No. 61/436,851, filed on Jan. 27, 2011.

(51) Int. Cl.
| | |
|---|---|
| *A61K 31/37* | (2006.01) |
| *A61K 31/665* | (2006.01) |
| *A61K 31/7048* | (2006.01) |
| *A61K 45/06* | (2006.01) |
| *A61K 36/48* | (2006.01) |

(52) U.S. Cl.
CPC .......... *A61K 31/37* (2013.01); *A61K 45/06* (2013.01); *A61K 36/48* (2013.01)
USPC ............................................ 514/27; 435/375

(58) Field of Classification Search
CPC ........ A61K 31/37; A61K 45/06; A61K 36/48
USPC ............................................ 514/27; 435/375
See application file for complete search history.

(56) References Cited

U.S. PATENT DOCUMENTS

| | | |
|---|---|---|
| 3,155,591 A | 11/1964 | Hilfer |
| 3,755,560 A | 8/1973 | Dickert et al. |
| 3,929,678 A | 12/1975 | Laughlin et al. |
| 3,959,461 A | 5/1976 | Bailey et al. |
| 4,139,619 A | 2/1979 | Chidsey et al. |
| 4,278,656 A | 7/1981 | Nagai et al. |
| 4,369,174 A | 1/1983 | Nagai et al. |
| 4,387,090 A | 6/1983 | Bolich, Jr. |
| 4,421,769 A | 12/1983 | Dixon et al. |
| 4,684,635 A | 8/1987 | Orentreich et al. |
| 4,959,393 A | 9/1990 | Torihara et al. |
| 5,011,681 A | 4/1991 | Ciotti et al. |
| 5,073,371 A | 12/1991 | Turner et al. |
| 5,073,372 A | 12/1991 | Turner et al. |
| 5,120,532 A | 6/1992 | Wells et al. |
| 5,132,740 A | 7/1992 | Okamoto et al. |
| 5,151,209 A | 9/1992 | McCall et al. |
| 5,151,210 A | 9/1992 | Steuri et al. |
| 5,214,028 A | 5/1993 | Tomita et al. |
| 5,352,440 A | 10/1994 | Gilchrest et al. |
| 5,389,611 A | 2/1995 | Tomita et al. |
| 5,532,001 A | 7/1996 | Gilchrest et al. |
| 5,554,359 A | 9/1996 | Fuller et al. |
| 5,580,549 A | 12/1996 | Fukuda et al. |
| 5,691,380 A | 11/1997 | Mason et al. |
| 5,968,528 A | 10/1999 | Deckner et al. |
| 6,123,959 A | 9/2000 | Jones et al. |
| 6,132,740 A | 10/2000 | Hu |
| 6,139,854 A | 10/2000 | Kawato |
| 6,159,482 A | 12/2000 | Tuloup et al. |
| 6,750,229 B2 | 6/2004 | Seiberg et al. |
| 6,995,804 B2 | 2/2006 | Kwon et al. |
| 8,563,754 B2 * | 10/2013 | Orlow et al. ................... 549/387 |
| 2008/0305059 A1 * | 12/2008 | Chaudhuri ....................... 424/62 |

(Continued)

FOREIGN PATENT DOCUMENTS

| | | |
|---|---|---|
| EP | 0997140 | 5/2000 |
| JP | 59157009 | 9/1984 |

(Continued)

OTHER PUBLICATIONS

Stanley et al. Citrus coumarins. J Agr Food Chem 19:1106-1110, 1971.*

(Continued)

*Primary Examiner* — Brandon Fetterolf
*Assistant Examiner* — Yih-Horng Shiao
(74) *Attorney, Agent, or Firm* — Klauber & Jackson LLC

(57) ABSTRACT

Provided are coumarin compounds of formula I, for example, robustic acid methyl ether, and the use of such compounds and compositions thereof to modulate (e.g., inhibit) melanogenesis and pigmentation.

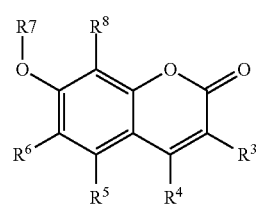

wherein $R^3$, $R^4$, $R^5$, $R^6$, $R^7$ and $R^8$ are described herein. Also provided are plant extracts containing a compound of formula I, and the use of such a plant extract to modulate (e.g., inhibit) melanogenesis and pigmentation. The compound or plant extract may be prepared as pharmaceutical and cosmetic compositions, and may be used for the prevention and treatment of conditions that are related to aberrant melanogenesis activity.

22 Claims, 3 Drawing Sheets

(56) References Cited

U.S. PATENT DOCUMENTS

| | | | |
|---|---|---|---|
| 2011/0190229 A1* | 8/2011 | Orlow et al. ................. | 514/27 |
| 2012/0196926 A1* | 8/2012 | Orlow ........................ | 514/452 |
| 2012/0237623 A1* | 9/2012 | Ptchelintsev et al. ......... | 424/757 |

FOREIGN PATENT DOCUMENTS

| | | |
|---|---|---|
| JP | 5221846 | 8/1993 |
| JP | 5320025 | 12/1993 |
| JP | 7206753 | 8/1995 |
| JP | 7242687 | 9/1995 |
| JP | 7324023 | 12/1995 |
| JP | 8012552 | 1/1996 |
| JP | 8012554 | 1/1996 |
| JP | 8012557 | 1/1996 |
| JP | 8012560 | 1/1996 |
| JP | 8012561 | 1/1996 |
| JP | 8134090 | 5/1996 |
| JP | 8168378 | 7/1996 |
| JP | 8277225 | 10/1996 |
| JP | 9002967 | 1/1997 |
| JP | 9295927 | 11/1997 |
| JP | 10081626 | 3/1998 |
| JP | 100072330 | 3/1998 |
| JP | 10101543 | 4/1998 |
| JP | 11071231 | 3/1999 |
| JP | 11079934 | 3/1999 |
| JP | 11246344 | 9/1999 |
| JP | 11246347 | 9/1999 |
| JP | 080023 | 3/2000 |
| JP | 095663 | 4/2000 |
| JP | 159681 | 6/2000 |
| JP | 247907 | 9/2000 |
| WO | 9909011 | 2/1999 |
| WO | 9932077 | 7/1999 |
| WO | 9964025 | 12/1999 |
| WO | 0056702 | 9/2000 |
| WO | 0062742 | 10/2000 |
| WO | 0076473 | 12/2000 |
| WO | 0101131 | 1/2001 |
| WO | 02098347 | 12/2002 |

OTHER PUBLICATIONS

Pieroni et al. Ethnopharmacognostic survey on the natural ingredients used in folk cosmetics, cosmeceuticals and remedies for healing skin diseases in the inland Marches, Central-Eastern Italy. J Ethnopharmacol 91:331-344, 2004.*
Laupattarakasem et al. Anti-Inflammatory Isoflavonoids from the Stems of *Derris scandens*. Planta Med 70:496-501, 2004.*
Orlow, 1998, in the Pigmentary System: Physiology and Pathophysiology 97, Oxford University Press, New York, Nordlund et al., eds.
Bundgard, H., "Design of Prodrugs", pp. 7-9, 21-24, Elsevier, Amsterdam 1985.
Remington's Pharmaceutical Sciences, 17th Ed., Mack Publishing Company, Easton, PA, 1990 (supra).
Pharmaceutical Dosage Forms and Drug Delivery Systems, 6th Ed., Williams & Wilkins (1995).
McCutcheon's Detergents and Emulsifiers, North American Edition, pp. 317-324 (1986), published by Allured Publishing Corporation.
McCutcheon's, Detergents & Emulsifiers, North American Edition (1979), M.C. Publishing Co.
Schwartz, et al., "Surface Active Agents, Their Chemistry and Technology," New York: Interscience Publishers, 1949.
Sagarin, Cosmetics, Science and Technology, 2nd Edition, vol. 1, p. 32-43 (1972).
Sagarin, Cosmetics, Science and Technology, 2nd Edition, vol. 1, pp. 72-78 (1972).

* cited by examiner

SCANDENIN

ROBUSTIC ACID METHYL ETHER

COUMOPHOS

COUMARIN COMPOUNDS AS MELANOGENESIS MODIFIERS AND USES THEREOF

RELATED APPLICATION

The present application claims the benefit under 35 U.S.C. §119 of U.S. Provisional Application Ser. No. 61/436,851 filed Jan. 27, 2011. The content of said provisional application is hereby incorporated by reference in its entirety.

GOVERNMENT RIGHTS

This invention was made in part with government support under Grant No. AR41880 awarded by the National Institute of Health. Accordingly, the United States Government has certain rights in the invention.

FIELD OF THE INVENTION

The present invention relates to the identification of coumarin compounds that modulate melanin synthesis (melanogenesis), and the use of such compounds and compositions thereof to modify (e.g., inhibit) melanin production. This invention also relates to methods for preventing and/or treating conditions that are causally related to aberrant melanogenesis activity, such as comprising (but not limited to) pigmentation abnormalities and hyperpigmentation, using the compounds of the invention. It is to be understood that such compounds may be used either alone or in combination with other compounds having the activity set forth herein.

BACKGROUND OF THE INVENTION

Several publications and patent documents are referenced in this application in order to more fully describe the state of the art to which this disclosure pertains. The disclosure of each of these publications and documents is expressly incorporated by reference herein.

Melanocytes synthesize melanin inside specialized organelles called melanosomes (reviewed in Orlow, 1998, in The Pigmentary System: Physiology and Pathophysiology 97, Oxford University Press, New York, Nordlund et al., eds). Melanosomes are formed by the fusion of two types of vesicles. Melanin is a dark biological pigment (biochrome) found in the skin, hair, feathers, scales, eyes, and some internal membranes of many animals that confers protection against ultraviolet radiation. See http://www.britannica.com/eb/topic?idxStructId=460219&typeId=13; http://www.britannica.com/eb/topic?idxStructId=126546&typeId=13; http://www.britannica.com/eb/article-9109619.

Melanism refers to the deposition of melanin in the tissues of living animals, the chemistry of which depends on the metabolism of the amino acid tyrosine. More specifically, melanins are formed as an end product during metabolism of the amino acid tyrosine. See http://www.britannica.com/eb/topic?idxStructId=611971&typeId=13. Defects in the production of melanin and deposition of melanin (i.e., melanism) can result in pigmentation deficiencies such as albinism.

The ability to control melanin synthesis, which in turn, alters skin pigmentation, may be used advantageously to address a variety of health-related conditions, as well as cosmetic objectives. Decreasing pigmentation is a desirable outcome in the treatment of disorders such as melasma, chloasma, post-inflammatory hyperpigmentation, solar lentigines, and the like.

The ability to modify skin coloring has generated considerable interest in many cultures. Inappropriate production or overproduction of melanin is considered a cosmetic problem by many individuals. In particular, the ability to remove hyperpigmentation, such as that found in age spots, freckles or aging skin generally, is of interest to individuals desiring a uniform complexion. Moreover, since chloasma, freckles, and pigmentary deposits that appear after over-exposure to the sun tend to occur or increase in frequency in middle aged and elderly individuals, such concerns are amplified in aging individuals. Indeed, with advancing years, these pigment deposits typically take longer to disappear and are more likely to become permanent. In certain areas of the world, general body whitening is also desirable.

A number of products have been developed to affect a decrease in skin pigmentation. One such product contains hydroquinone, a well known active substance for skin de-pigmentation, as described in U.S. Pat. No. 6,139,854. Hydroquinone can, however, have serious side effects if applied over a long period of time. The application of hydroquinone to skin may, for example, lead to permanent de-pigmentation, which results in increased photosensitivity of the skin upon exposure to ultraviolet light. Hydroquinone can be administered in combination with cortisone (which can thin the skin and cause other problems following facial administration), retinoic acid (an irritant), or glycolic acid (an irritant) to increase the efficacy of hydroquinone.

A variety of other substances have been proposed for use as regulators of skin pigmentation. Almost all of these substances work by either bleaching existing pigment or preventing new pigment synthesis by inhibiting the activity of tyrosinase, the principal rate limiting enzyme in the production of melanin. U.S. Pat. No. 6,123,959, for example, describes the use of aqueous compositions comprising liposomes and at least one competitive inhibitor of an enzyme involved in melanin synthesis. U.S. Pat. No. 5,132,740 describes the use of certain resorcinol derivatives as skin lightening agents. WO 99/64025 describes compositions for skin lightening which contain tyrosinase inhibiting extracts from dicotyledonous plant species indigenous to Canada. U.S. Pat. No. 5,580,549 describes an external preparation for skin lightening comprising 2-hydroxybenzoic acid derivatives and salts thereof as inhibitors of tyrosinase. WO 99/09011 describes an agent for inhibiting skin erythema and/or skin pigmentation, containing at least one carbostyril derivative and salts thereof. U.S. Pat. Nos. 5,214,028 and 5,389,611, describe lactoferrin hydrolyzates for use as tyrosinase inhibitory agents.

In WO 02 98347, Manga describes methods for identifying compounds that alter melanogenesis in melanogenic cells, more particularly, compounds that inhibit or enhance P protein function. This method is based, in part, on the observation that P protein function is required for proper cellular localization of tyrosinase and other melanosomal proteins, and is required for both full tyrosinase activity and melanogenesis in melanogenic cell types.

Orlow et al. describe screens for identifying compounds that inhibit or increase melanogenesis in melanogenic cells. See WO 01 1131. These studies were based upon the discovery that some compounds that inhibit melanogenesis do so by causing a mislocalization of tyrosinase, the key enzyme in melanin synthesis.

Other studies are directed to methods and compositions for increasing melanogenesis. U.S. Pat. No. 5,352,440, for example, is directed to increasing melanin synthesis in melanocytes and increasing pigmentation by administration of certain diacylglycerol compounds. U.S. Pat. No. 5,532,001 is directed to increasing pigmentation in mammalian skin via administration of certain DNA fragments. U.S. Pat. No. 5,554,359 is directed to increasing levels of melanin in melanocytes by administration of lysosomotropic agents. U.S. Pat. Nos. 6,750,229 and 6,995,804 are directed to the identification of protease-activated receptor-2 (PAR-2) pathway and nitric oxide synthesis modulators, respectively, and their use in modulating pigmentation levels.

As described above, many methods have been proposed to achieve desired pigmentation levels of the skin. Such methods have included kojic acid, hydroquinone, retinoids and other chemical compounds for depigmentation purposes. The value of many of these compounds and compositions thereof, however, has been questionable. Precise application of all these compounds is necessary in order to achieve the desired result since a distinct line of demarcation between treated versus non-treated areas of the skin is frequently apparent. Moreover, many of these compounds cause skin irritation and, therefore, use of such compounds has undesirable side effects, particularly for long-term use.

SUMMARY OF THE INVENTION

The present invention is directed to compounds that may be identified by cell-based assays, which compounds control melanogenesis. In brief, compounds were screened in cell-based assays to identify compounds capable of controlling, and particularly, inhibiting melanogenesis. Details pertaining to the screening assays are described in the Examples below. The results of the screening assays identified a plurality of compounds that modify (i.e. inhibit) melanogenesis, some of which were not previously known to exhibit such activity and others of which are known to affect melanogenesis. Notably, the confirmation of the activity of known modifiers of melanogenesis in the present screen corroborates the validity of the techniques and experimental approach.

As such, disclosed herein are embodiments directed to the identification of previously unidentified coumarin melanogenesis inhibitors, and their use in controlling (e.g. reducing) pigmentation in in vitro and in vivo applications. The disclosure further provides methods of administering the coumarin melanogenesis inhibitors as an extract, or as a purified compound. The method optionally includes obtaining a quantity of plant matter from a plant of the derris family, optionally comminuting the plant matter, contacting said plant matter with an extraction medium, and separating the plant matter from the extraction medium.

The novel melanogenesis modifiers include compounds represented by formula I:

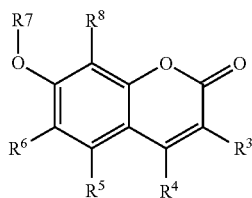

wherein $R^3$ is selected from H, halo, substituted or unsubstituted alkyl, substituted or unsubstituted alkenyl, or substituted or unsubstituted aryl; and substituted or unsubstituted heteroaryl;

$R^4$ is selected from H, halo, hydroxy, alkoxy, alkenyloxy, substituted or unsubstituted alkyl, substituted or unsubstituted alkenyl, and substituted or unsubstituted phenyl;

each $R^5$, $R^6$, and $R^8$ is independently selected from H, halo, hydroxy, alkoxy, alkenyloxy, substituted or unsubstituted alkyl, substituted or unsubstituted alkenyl, and substituted or unsubstituted phenyl;

$R^7$ is selected from H, halo, hydroxy, alkoxy, alkenyloxy, substituted or unsubstituted alkyl, substituted or unsubstituted alkenyl, or heterocycloalkyl; or $R^7$ is —P(=O)(alkoxy)$_2$, or —P(=S)(alkoxy)$_2$; or $R^6$ and $R^7$ or $R^7$ and $R^8$ are joined to form a 5- or 6-membered heterocycloalkyl or heterocycloalkenyl; and the heterocycloalkyl or heterocycloalkenyl is unsubstituted or substituted with one more groups selected from alkyl, alkenyl, hydroxyalkyl, acyloxyalkyl, hydroxy, and alkoxy; and provided that
i) when $R^3$ is H; then $R^8$ is substituted or unsubstituted alkenyl;
ii) the compound is other than robustic acid; and
iii) when each of $R^3$, $R^4$, $R^5$, and $R^6$ is H; and $R^8$ is 3-methylbut-2-enyl; then $R^7$ is other than Me;

or pharmaceutically acceptable salts, solvates, isomers, tautomers, metabolites, analogs, isotopic variants or prodrugs thereof.

In one particular embodiment, with respect to formula I, the compound is formula VIIa (robustic acid methyl ether):

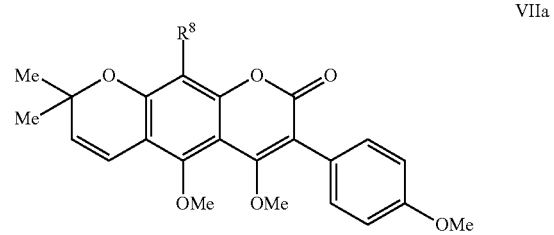

or a pharmaceutically acceptable salts, solvates, isomers, tautomers, metabolites, analogs, isotopic variants or prodrugs thereof.

In another particular embodiment, with respect to formula I, the compound is formula VIIb (scandenin):

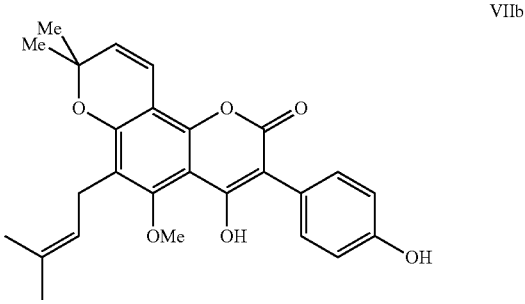 [SMILES: COc1c(CC=C(C)C)c2c(c3oc(=O)c(-c4ccc(O)cc4)c(O)c13)C=CC(C)(C)O2]

or a pharmaceutically acceptable salts, solvates, isomers, tautomers, metabolites, analogs, isotopic variants or prodrugs thereof.

Another aspect of the invention provides a method for preventing inhibiting melanogenesis comprising administering an effective amount of a compound of formula I.

Another aspect of the invention provides a method for promoting skin lightening comprising administering an effective amount of a compound of formula I.

In another aspect, the invention provides methods for inhibiting melanogenesis using the compounds of formulae I-VIIb.

In another aspect, the invention provides methods for inhibiting melanogenesis using a plant extract containing compounds of formula I. In one embodiment the plant extract is derived from *derris scandens*.

In another aspect, the invention provides methods for promoting skin lightening using the compounds of formulae I-VIIb.

In another aspect, the invention provides methods for promoting skin lightening using a plant extract containing compounds of formula I. In one embodiment the plant extract is derived from *derris scandens*.

With respect to in vitro applications, test-tube based and additional cell-based assays may be used to test the ability of modified versions and/or compounds to alter melanogenesis. In vivo applications are directed to the administration of at least one of the novel melanogenesis modifier compounds to a subject desirous thereof or in need thereof to control and/or to reduce pigmentation levels for prophylactic, therapeutic and/or cosmetic purposes.

In accordance with the disclosed embodiments, a method is presented for effecting changes in mammalian skin pigmentation comprising topical application of at least one coumarin compound or a composition thereof to the skin of a mammal. Compositions disclosed herein may contain one or more of the coumarin compounds which have been identified as modifiers of melanogenesis.

More specifically and with respect to those compounds capable of reducing or inhibiting melanogenesis, the disclosed embodiments encompass a method for decreasing pigmentation in mammalian skin, hair or wool, and/or enhancing the brightening thereof, which comprises topically administering to the mammal an effective amount of one or more compounds described herein as a melanogenesis modifier.

In a particular embodiment, a melanogenesis modifier as disclosed herein or a composition thereof may be applied to sites of hyperpigmentation including, without limitation, age spots, freckles, drug-induced hyperpigmentation, post-inflammatory hyperpigmentation as seen in acne, seborrheic keratoses, melasma and chloasma. For some individuals, body whitening over a larger area of the skin is desirable and may be achieved with a more generalized application of a melanogenesis inhibitor disclosed herein or a composition thereof.

In a further aspect, the disclosed embodiments provide compositions, including cosmetic formulations, comprising a compound or compounds disclosed herein, and a suitable biocompatible or bioinert carrier, excipient or diluent. In this aspect, the cosmetic or pharmaceutical composition can comprise one or more of the compounds described herein. Moreover, the compounds disclosed herein are useful in cosmetic and/or pharmaceutical compositions and treatment methods disclosed herein, are all pharmaceutically and/or cosmetically acceptable as prepared and used.

In a further aspect, disclosed herein are compositions comprising a combination of a compound described herein with various additional compounds or agents, including compounds or agents that may have a like effect on melanogenesis, such as, for example, other skin lighteners, skin brightening agents or skin bleaching agents. In some embodiments, the additional compound or agent may be a skin care active agent, such as an abrasive, an absorbent, an astringent, an aesthetic component, such as fragrances, pigments, colorings/colorants, essential oils, skin sensates, astringents and other aesthetic components, an antioxidant, a reducing agent, a sequestrant, a skin bleaching or lightening agent, a skin conditioning agent, for example humectants and emollients, a skin soothing agent, a skin healing agent, such as pathenol and derivatives, aloe vera, pantothenic acid, allantoin, bisbolol, dipotassium glycyrrhizinate, skin treating agents, vitamins and derivatives, such as a retinoid, or mixtures thereof. In some embodiments, the retinoid is retinol, retinal, retinol esters, retinyl propionate, retinoic acid, retinyl palmitate, or mixtures thereof. In this aspect, the pharmaceutical and/or cosmetic compositions can comprise one or more of the compounds described herein. Moreover, the compounds are useful in the pharmaceutical and/or cosmetic compositions and treatment methods disclosed herein, are all pharmaceutically and/or cosmetically acceptable as prepared and used.

Also provided are methods for inhibiting melanogenesis by melanocytes, comprising administering to the melanocytes or skin tissue an effective amount of a plant extract containing a melanogenesis inhibitor. In some embodiments, the melanogenesis inhibitor is a coumarin melanogenesis inhibitor as in Formula I. In some embodiments, the melanogenesis inhibitor is scandenin or a scandenin derivative. In some embodiments, the melanogenesis inhibitor is robustic acid methyl ether or a robustic acid methyl ether derivative. In some embodiments, the melanocytes are mammalian melanocytes. In some embodiments, the skin tissue is human skin including but not limited to African American, Asian and Caucasian skin equivalents. In some embodiments, the plant extract is derived from a plant of the derris family. In some embodiments, the plant extract is derived from *derris scandens* (also known as khao lor).

In some embodiments, also provided are plant extracts containing a prophylactically, therapeutically and/or cosmetically effective amount of a melanogenesis inhibitor for use as an inhibitor of melanogenesis. The plant extract can be used as a pharmaceutical, a medicament or as a cosmetic agent. In some embodiments, the plant extract is substantially purified or partially purified for concentration of the melanogenesis inhibitor. In other embodiments, the plant extract may be substantially liquefied or partially liquefied for administration to a patient in need thereof. The plant extract may also be processed to remove particulate matter prior to administration. In some embodiments, the melanogenesis inhibitor is scandenin or a scandenin-derivative.

Also provided are uses of a plant extract as disclosed herein for the manufacture of a medicament or cosmetic agent to treat a disease, condition or effect for which a melanogenesis inhibitor is indicated. The diseases, condition or effect that can be prevented, treated, ameliorated and/or managed by the subject compositions and methods include but are not limited to hyperpigmentation or uneven pigmentation disorders such as age spots, freckles, drug-induced hyperpigmentation, post-inflammatory hyperpigmentation as seen in acne, seborrheic keratoses, melasma and chloasma. In other embodiments, a topical formulation comprising a composition is provided for cosmetic and/or dermatological/pharmaceutical use, said composition comprising a plant extract containing a prophylactically, cosmetically or therapeutically effective amount of scandenin or robustic acid methyl ether. In some embodiments, the plant extract is derived from a plant of the derris family. In some embodiments, the plant extract is derived from *derris scandens* (also known as khao lor). In some embodiments, the plant extract is substantially purified or partially purified for concentration of the melanogenesis inhibitor. In other embodiments, the plant extract may be substantially liquefied or partially liquefied for administration to a patient in need thereof. The plant extract may also be processed to remove particulate matter prior to administration. In some embodiments, the melanogenesis inhibitor is scandenin or a scandenin derivative. In some embodiments, the melanogenesis inhibitor is robustic acid methyl ether or a robustic acid methyl ether derivative.

Also provided are methods for preventing, treating, ameliorating or managing a disease or condition involving undesired or aberrant melanogenesis, which comprises administering to a patient in need or desirous of such prevention, treatment, amelioration or management, a prophylactically or therapeutically effective melanogenesis-inhibiting amount of a plant extract containing a melanogenesis inhibitor. In some embodiments, the melanogenesis inhibitor is a coumarin melanogenesis inhibitor as in Formula I. In one embodiment, the melanogenesis inhibitor is scandenin or a scandenin derivative. In some embodiments, the melanogenesis inhibitor is robustic acid methyl ether or a robustic acid methyl ether derivative.

In yet another aspect, methods are provided for altering or restoring pigmentation in mammalian skin, hair, wool or fur comprising administering to the mammalian skin, hair, wool or fur an amount, which is effective to alter or restore pigmentation in mammalian skin, hair, wool or fur, of a plant extract containing scandenin. In still another aspect, also provided are methods of treatment of a mammal, including a human being, to treat a disease for which a melanogenesis inhibitor is indicated, including treating said mammal with an effective amount of a plant extract containing scandenin. In some embodiments, the plant extract is derived from a plant of the derris family. In some embodiments, the plant extract is derived from *derris scandens*. In some embodiments, the plant extract is substantially purified or partially purified for concentration of the melanogenesis inhibitor. In other embodiments, the plant extract may be substantially liquefied or partially liquefied for administration to a patient in need thereof. The plant extract may also be processed to remove particulate matter prior to administration. In some embodiments, the melanogenesis inhibitor is scandenin or a scandenin derivative.

In some embodiments of the subject methods, the melanogenesis-inhibitor containing plant extract is administered to lighten or reduce pigmentation levels. For example, the melanogenesis-inhibitor-containing plant extract is administered to lighten or reduce pigmentation levels of hyperpigmented sites on skin. In some embodiments, the melanogenesis inhibitor is scandenin or a scandenin derivative. In some embodiments, the plant extract is derived from a plant of the derris family. In some embodiments, the plant extract is derived from *derris scandens*. In some embodiments, the plant extract is substantially purified or partially purified for concentration of the melanogenesis inhibitor. In other embodiments, the plant extract may be substantially liquefied or partially liquefied for administration to a patient in need thereof. The plant extract may also be processed to remove particulate matter prior to administration. In some embodiments, the melanogenesis inhibitor is scandenin or a scandenin derivative. In some embodiments, the melanogenesis inhibitor is robustic acid methyl ether or a derivative.

In a further embodiment, combinations of a plant extract as disclosed herein and a like-acting agent are provided. The like acting agent can be selected from a cosmetic ingredient and/or a pharmacologically active agent. For example, the cosmetic ingredient may be a skin lightener or a sunscreen agent or an agent that increases skin cell turnover. The pharmacologically active agent can be selected from another melanogenesis inhibitor.

Another aspect encompasses a method for inhibiting melanogenesis by melanocytes comprising administering to the melanocytes an effective amount of a plant extract containing a melanogenesis-inhibitor in combination with a like-acting agent. In some embodiments, the plant extract is substantially purified or partially purified for concentration of the melanogenesis inhibitor. In other embodiments, the plant extract may be substantially liquefied or partially liquefied for administration to a patient in need thereof. The plant extract may also be processed to remove particulate matter prior to administration. In some embodiments, the melanogenesis inhibitor is scandenin or a scandenin derivative. In some embodiments, the melanogenesis inhibitor is robustic acid methyl ether or a robustic acid methyl ether derivative.

Also provided herein is a method for preventing, treating, ameliorating or managing a disease or condition involving undesired or aberrant melanogenesis, which comprises administering to a patient in need or desirous of such prevention, treatment, amelioration or management, a prophylactically or therapeutically effective melanogenesis-inhibiting amount of a plant extract in combination with a like-acting agent.

In still another aspect, also provided are methods of treatment of a mammal, including a human being, to treat a disease for which a melanogenesis inhibitor is indicated, including treating said mammal with an effective amount of a plant extract containing a melanogenesis-inhibitor in combination with a like-acting agent. In some embodiments, the plant extract is derived from a plant of the derris family. In some embodiments, the plant extract is derived from *Derris scandens*.

In another aspect, provided are methods for altering or restoring pigmentation in mammalian skin, hair, wool or fur comprising administering to the mammalian skin, hair, wool or fur an amount, which is effective to alter or restore pigmentation in mammalian skin, hair, wool or fur, of a plant extract containing a melanogenesis-inhibitor in combination with a like-acting agent.

In any of the above subject methods, the like acting agent can be selected from a cosmetic ingredient and a pharmacologically active agent. One example of a cosmetic ingredient is a skin lightener. The pharmacologically active agent can be selected from another melanogenesis inhibitor.

Other objects and advantages will become apparent to those skilled in the art from a consideration of the ensuing detailed description, which proceeds with reference to the following illustrative drawings.

DETAILED DESCRIPTION OF THE INVENTION

Definitions

Figure 1:
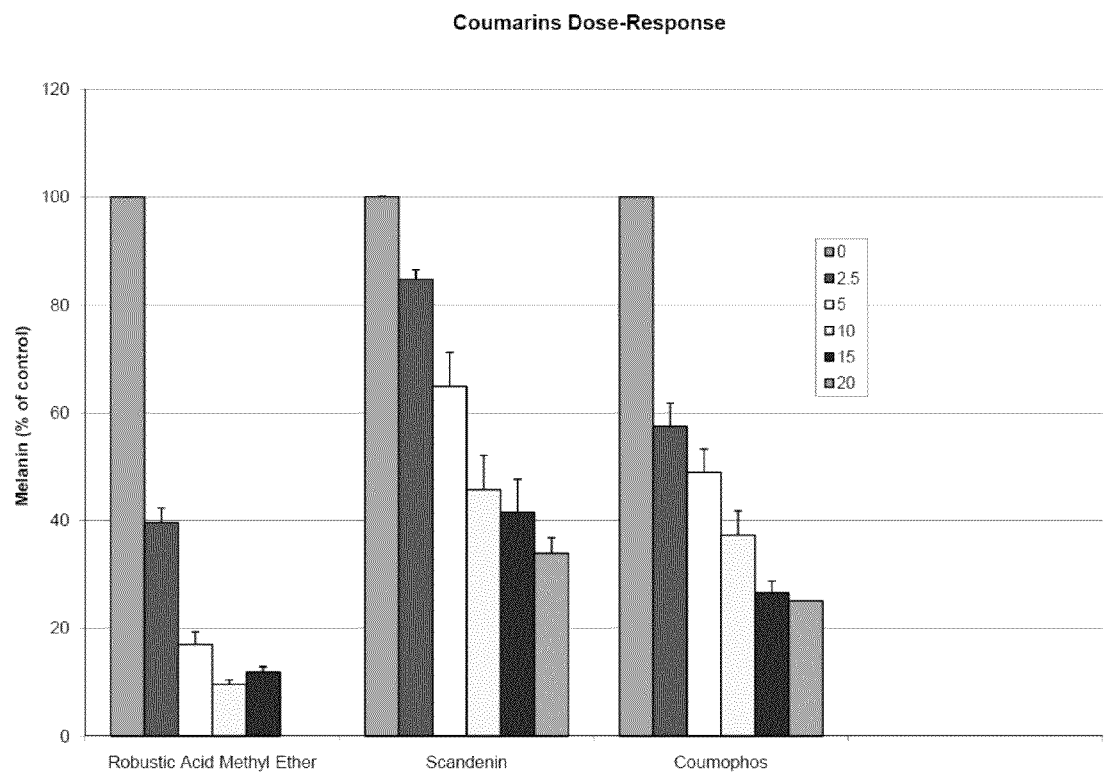
FIG. 1 is a graph of the results of comparative dose-response testing of compounds of the invention as inhibitors of melanin.
Figure 2:
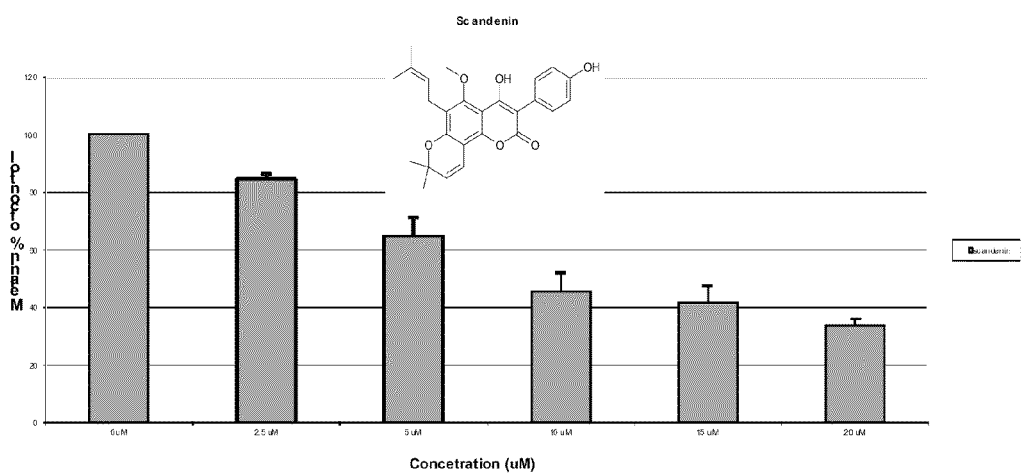
FIGS. 2-4 are graphs of individual dose response testing of particular compounds of the invention.
Figure 3:
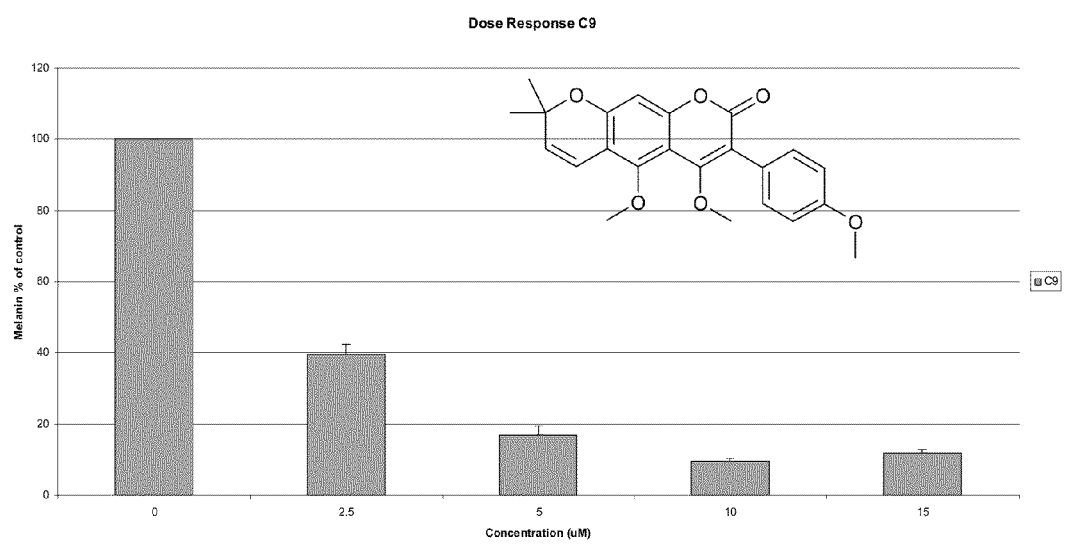
Figure 4:
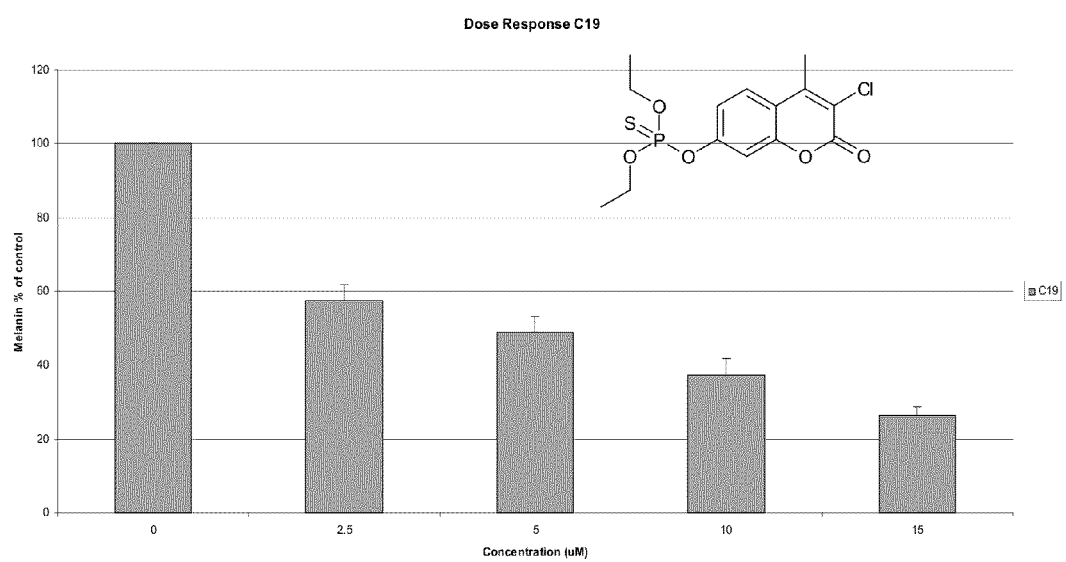

When describing the compounds, pharmaceutical and/or cosmetic compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

"Acyl" refers to a group or radical —C(O)R$^{20}$, where R$^{20}$ is hydrogen, substituted or unsubstituted alkyl, substituted or unsubstituted cycloalkyl, substituted or unsubstituted cycloheteroalkyl, substituted or unsubstituted aryl, substituted or unsubstituted arylalkyl, substituted or unsubstituted heteroalkyl, substituted or unsubstituted heteroaryl, substituted or unsubstituted heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a group or radical —NR$^{21}$C(O)R$^{22}$, where R$^{21}$ is hydrogen, substituted or unsubstituted alkyl, substituted or unsubstituted cycloalkyl, substituted or unsubstituted cycloheteroalkyl, substituted or unsubstituted aryl, substituted or unsubstituted arylalkyl, substituted or unsubstituted heteroalkyl, substituted or unsubstituted heteroaryl, substituted or unsubstituted heteroarylalkyl and R$^{22}$ is hydrogen, substituted or unsubstituted alkyl, substituted or unsubstituted alkoxy, substituted or unsubstituted cycloalkyl, substituted or unsubstituted cycloheteroalkyl, substituted or unsubstituted aryl, substituted or unsubstituted arylalkyl, substituted or unsubstituted heteroalkyl, substituted or unsubstituted heteroaryl or substituted or unsubstituted heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group or radical —OC(O)R$^{23}$ where R$^{23}$ is hydrogen, substituted or unsubstituted alkyl, substituted or unsubstituted aryl or substituted or unsubstituted cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR$^{24}$ where R$^{24}$ is alkyl. Particular alkoxy groups include, by way of example, substituted or unsubstituted methoxy, substituted or unsubstituted ethoxy, substituted or unsubstituted n-propoxy, substituted or unsubstituted isopropoxy, substituted or unsubstituted n-butoxy, substituted or unsubstituted tert-butoxy, substituted or unsubstituted sec-butoxy, substituted or unsubstituted n-pentoxy, substituted or unsubstituted n-hexoxy, substituted or unsubstituted 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NR$^{25}$C(O)R$^{26}$ where R$^{25}$ is hydrogen, substituted or unsubstituted alkyl, substituted or unsubstituted aryl or substituted or unsubstituted cycloalkyl, and R$^{26}$ is substituted or unsubstituted alkyl or substituted or unsubstituted cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like, and may be substituted or unsubstituted. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as substituted or unsubstituted methylene (—CH$_2$—), substituted or unsubstituted ethylene (—CH$_2$CH$_2$—), the substituted or unsubstituted propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include substituted or unsubstituted ethenyl (—CH═CH$_2$), substituted or unsubstituted n-propenyl (—CH$_2$CH═CH$_2$), substituted or unsubstituted isopropenyl (—C(CH$_3$)═CH$_2$), substituted or unsubstituted vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as substituted or unsubstituted ethenylene (—CH═CH—), substituted or unsubstituted propenylene isomers (e.g., —CH═CHCH$_2$— and —C(CH$_3$)═CH— and —CH═C(CH$_3$)—) and the like.

"Alkynyl" refers to acetylenically or alkynically unsaturated hydrocarbyl groups particularly having 2 to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include substituted or unsubstituted acetylenic, substituted or unsubstituted ethynyl (—C≡CH), substituted or unsubstituted propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group R$^{27}$—C(O)—, where R$^{27}$ is hydrogen or substituted or unsubstituted alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like, and may be substituted or unsubstituted. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second substituted or unsubstituted aryl ring or with a substituted or unsubstituted aliphatic ring.

"Alkaryl" refers to an aryl group, as defined above, substituted with one or more substituted or unsubstituted alkyl groups, as defined above.

"Aralkyl" or "arylalkyl" refers to an alkyl group, as defined above, substituted with one or more substituted or unsubstituted aryl groups, as defined above.

"Aryloxy" refers to substituted or unsubstituted —O-aryl groups wherein "aryl" is as defined above.

"Alkylamino" refers to the group alkyl-NR$^{28}$R$^{29}$, wherein each of R$^{28}$ and R$^{29}$ are independently selected from hydrogen and substituted or unsubstituted alkyl.

"Arylamino" refers to the group aryl-NR$^{30}$R$^{31}$, wherein each of R$^{30}$ and R$^{31}$ are independently selected from hydrogen, substituted or unsubstituted aryl and substituted or unsubstituted heteroaryl.

"Alkoxyamino" refers to a radical —N(H)OR$^{32}$ where R$^{32}$ represents a substituted or unsubstituted alkyl or substituted or unsubstituted cycloalkyl group as defined herein.

"Alkoxycarbonyl" refers to a substituted or unsubstituted radical —C(O)-alkoxy where alkoxy is as defined herein.

"Alkylarylamino" refers to a substituted or unsubstituted radical —NR$^{33}$R$^{34}$ where R$^{33}$ represents an alkyl or cycloalkyl group and R$^{34}$ is an aryl as defined herein.

"Alkylsulfonyl" refers to a substituted or unsubstituted radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a substituted or unsubstituted radical —S(O)R$^{35}$ where R$^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a substituted or unsubstituted radical —SR$^{35}$ where R$^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R$^{36}$)$_2$ where each R$^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R$^{36}$)$_2$ is an amino group.

"Aminocarbonyl" refers to the group —C(O)NR$^{37}$R$^{37}$ where each R$^{37}$ is independently hydrogen, substituted or unsubstituted alkyl, substituted or unsubstituted aryl and substituted or unsubstituted cycloalkyl, or where the R$^{37}$ groups are joined to form an alkylene group.

"Aminocarbonylamino" refers to the group —NR$^{38}$C(O)NR$^{38}$R$^{38}$ where each R$^{38}$ is independently hydrogen, substituted or unsubstituted alkyl, substituted or unsubstituted aryl or substituted or unsubstituted cycloalkyl, or where two R groups are joined to form an alkylene group.

"Aminocarbonyloxy" refers to the group —OC(O)NR$^{39}$R$^{39}$ where each R$^{39}$ is independently hydrogen, substituted or unsubstituted alkyl, substituted or unsubstituted aryl or substituted or unsubstituted cycloalkyl, or where the R groups are joined to form an alkylene group.

"Arylalkyloxy" refers to a substituted or unsubstituted —O-arylalkyl radical where arylalkyl is as defined herein.

"Arylamino" means a substituted or unsubstituted radical —NHR$^{40}$ where R$^{40}$ represents an aryl group as defined herein.

"Aryloxycarbonyl" refers to a substituted or unsubstituted radical —C(O)—O-aryl where aryl is as defined herein.

"Arylsulfonyl" refers to a r substituted or unsubstituted radical —S(O)$_2$R$^{41}$ where R$^{41}$ is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like, and may be substituted or unsubstituted. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like, and may be substituted or unsubstituted. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N($R^{42}$)$_2$ where each $R^{42}$ group is independently hydrogen, substituted or unsubstituted alkyl, substituted or unsubstituted cycloalkyl or substituted or unsubstituted aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like, and may be substituted or unsubstituted.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —O$R^{43}$ where $R^{43}$ is substituted or unsubstituted cycloalkyl. Such cycloalkoxy groups include, by way of example, substituted or unsubstituted cyclopentoxy, substituted or unsubstituted cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as substituted or unsubstituted cyclohexenyl, substituted or unsubstituted cyclopentenyl, substituted or unsubstituted cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a substituted or unsubstituted cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —N$R^{44}R^{45}$ where $R^{44}$ and $R^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C═C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to —X, —$R^{46}$, —O$^-$, ═O, —O$R^{46}$, —S$R^{46}$, —S$^-$, ═S, —N$R^{46}R^{47}$, ═N$R^{46}$, —CX$_3$, —CF$_3$, —CN, —OCN, —SCN, —NO, —NO$_2$, ═N$_2$, —N$_3$, —S(O)$_2$O$^-$, —S(O)$_2$OH, —S(O)$_2R^{46}$, —OS(O$_2$)O$^-$, —OS(O)$_2R^{46}$—P(O)(O$^-$)$_2$, —P(O)(O$R^{46}$)(O$^-$), —OP(O)(O$R^{46}$)(O$R^{47}$), —C(O)$R^{46}$, —C(S)$R^{46}$, —C(O)O$R^{46}$, —C(O)N$R^{46}R^{47}$, —C(O)O$^-$, —C(S)O$R^{46}$, —N$R^{48}$C(O)N$R^{46}R^{47}$, —N$R^{48}$C(S)N$R^{46}R^{47}$, —N$R^{49}$C(N$R^{48}$)N$R^{46}R^{47}$ and —C(N$R^{48}$)N$R^{46}R^{47}$, where each X is independently a halogen; each $R^{46}$, $R^{47}$, $R^{48}$ and $R^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —N$R^{50}R^{51}$, —C(O)$R^{50}$ or —S(O)$_2R^{50}$ or optionally $R^{50}$ and $R^{51}$ together with the atom to which they are both attached form a cycloheteroalkyl or substituted cycloheteroalkyl ring; and $R^{50}$ and $R^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

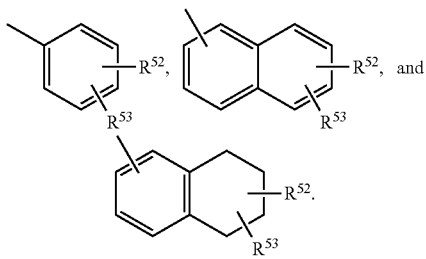

In these formulae one of $R^{52}$ and $R^{53}$ may be hydrogen and at least one of $R^{52}$ and $R^{53}$ is each independently selected from alkyl, alkenyl, alkynyl, cycloheteroalkyl, alkanoyl, alkoxy, aryloxy, heteroaryloxy, alkylamino, arylamino, heteroarylamino, $NR^{54}COR^{55}$, $NR^{54}SOR^{55}$, $NR^{54}SO_2R^{57}$, COOalkyl, COOaryl, $CONR^{54}R^{55}$, $CONR^{54}OR^{55}$, $NR^{54}R^{55}$, $SO_2NR^{54}R^{55}$, S-alkyl, S-alkyl, SOalkyl, $SO_2$alkyl, Saryl, SOaryl, $SO_2$aryl; or $R^{52}$ and $R^{53}$ may be joined to form a cyclic ring (saturated or unsaturated) from 5 to 8 atoms, optionally containing one or more heteroatoms selected from the group N, O or S. $R^{54}$, $R^{55}$, and $R^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

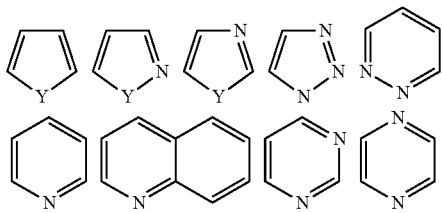

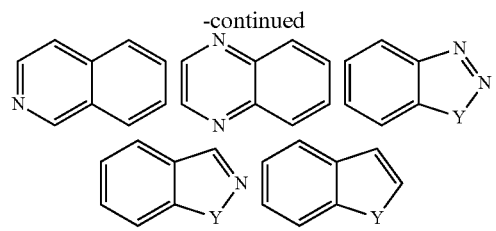

wherein each Y is selected from carbonyl, N, $NR^{58}$, O, and S; and $R^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

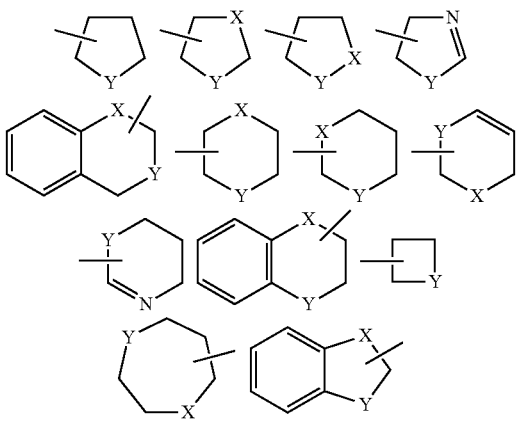

wherein each X is selected from $CR^{58}$, $CR^{58}{}_2$, $NR^{58}$, O and S; and each Y is selected from $NR^{58}$, O and S; and $R^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

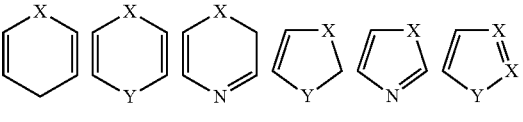

wherein each X is selected from $CR^{58}$, $CR^{58}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

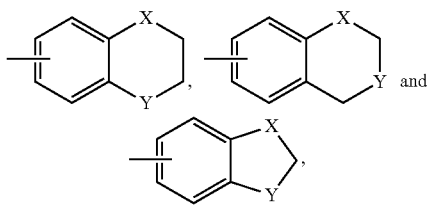

wherein each X is selected from $CR^{58}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an $R^4$ in a $R^4C$ group present as substituents directly on the ring or rings of the compounds disclosed herein, or that may be present as a substituent in any "substituted" aryl and aliphatic groups present in the compounds.

Examples of hetero substituents include:
-halo,
—$NO_2$, —$NH_2$, —$NHR^{59}$, —$N(R^{59})_2$,
—NRCOR, —$NR^{59}SOR^{59}$, —$NR^{59}SO_2R^{59}$, OH, CN,
—$CO_2H$,
—$R^{59}$—OH, —O—$R^{59}$, —$COOR^{59}$,
—$CON(R^{59})_2$, —$CONROR^{59}$,
—$SO_3H$, —$R^{59}$—S, —$SO_2N(R^{59})_2$,
—$S(O)R^{59}$, —$S(O)_2R^{59}$ wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

"Dihydroxyphosphoryl" refers to the substituted or unsubstituted radical —$PO(OH)_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the substituted or unsubstituted radical —$PO(OH)NH_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the substituted or unsubstituted group —$SR^{60}$ where $R^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the substituted or unsubstituted radical HS—. "Substituted sulfanyl" refers to a radical such as RS— wherein R is any substituent described herein.

"Sulfonyl" refers to the divalent substituted or unsubstituted radical —$S(O_2)$—. "Substituted sulfonyl" refers to a radical such as $R^{61}$—$(O_2)S$— wherein $R^{61}$ is any substituent described herein. "Aminosulfonyl" or "Sulfonamide" refers to the radical $H_2N(O_2)S$—, and "substituted aminosulfonyl" "substituted sulfonamide" refers to a radical such as $R^{62}_2N(O_2)S$— wherein each $R^{62}$ is independently any substituent described herein.

"Sulfone" refers to the substituted or unsubstituted group —$SO_2R^{63}$. In particular embodiments, $R^{63}$ is selected from H, lower alkyl, alkyl, aryl and heteroaryl.

"Thioaryloxy" refers to the substituted or unsubstituted group —$SR^{64}$ where $R^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

As used herein, "mammal" refers to any member of the higher vertebrate animals comprising the class Mammalia, which includes, but is not limited to, humans.

As used herein, the term "melanogenesis inhibitor" is used to describe a compound identified herein as possessing the ability to inhibit melanogenesis in a melanocyte.

As used herein, an "amount effective" shall mean an amount sufficient to cover the region of skin, hair, fur, or wool surface where a change in pigmentation is desired.

"Pharmaceutically acceptable" means approved by a regulatory agency of the Federal or a state government or listed in the U.S. Pharmacopoeia or other generally recognized pharmacopoeia for use in animals, and more particularly in humans.

"Cosmeceutically acceptable" means suitable for cosmetic applications, including topical application of the compositions disclosed herein in the absence of significant adverse side effects upon application of the composition or compounds disclosed herein. Other applications include skin care applications, including but not limited to lotions, cream, cleansing creams or lotions, soaps and other cleansers, antiperspirant and/or deodorants, makeup products, such as face powders, foundations, rouge, eye shadow, mascara, eyeliner or lipstick, sun protection products, such as sunscreen or other UV-protective cosmetics, lotions or creams, hairdressing products, such as shampoo, rinses, or treatment setting agents. The phrases "pharmaceutically acceptable" and "cosmeceutically acceptable" are not meant to imply mutual exclusiveness in all applications. In some embodiments, a composition may be both "pharmaceutically acceptable" and "cosmeceutically acceptable," dependent upon the need and course of action of the compositions disclosed herein.

"Pharmaceutically acceptable salt" refers to a salt of a compound disclosed herein that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. In some embodiments, a "pharmaceutically acceptable salt" may also be used in conjunction with cosmeceutically-acceptable compositions.

The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like. In some embodiments, a "pharmaceutically acceptable cation" may also be used in conjunction with cosmeceutically-acceptable compositions.

"Pharmaceutically acceptable vehicle" refers to a diluent, adjuvant, excipient or carrier with which a disclosed compound is administered. In some embodiments, a "pharmaceutically acceptable vehicle" may also be used in conjunction with cosmeceutically-acceptable compositions.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of disclosed compounds, which have cleavable groups and become by solvolysis or under physiological conditions of compounds which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds disclosed herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same. In a still further embodiment, "treating" or "treatment" refers to administration of the compound or compositions disclosed herein for cosmetic purposes.

Other derivatives of the disclosed compounds have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the disclosed compounds are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the disclosed compounds herein.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the disclosed compounds may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the contemplated compounds.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The disclosed compounds may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

As described herein, disclosed are embodiments relating to the identification of compounds that control melanin (inhibit) synthesis (melanogenesis), and the use of such compounds and compositions thereof to modify (e.g., inhibit) melanin production. Also related are methods for preventing and/or treating conditions that are causally related to aberrant melanogenesis activity, comprising (but not limited to) aberrant pigmentation, including hyperpigmentation of all etiologies, uneven pigmentation, and the like, using the compounds and compositions disclosed herein.

Accordingly, a plurality of compounds has been identified that are capable of controlling, and particularly, inhibiting melanogenesis. These compounds, which were not previously identified as possessing such a capability, are listed herein and referred to as novel melanogenesis modifiers. Accordingly, the compounds and compositions disclosed herein are directed to their use in modifying pigmentation in in vitro and in vivo applications. With respect to in vitro applications, test-tube based and additional cell-based assays may be used to test the ability of modified versions and/or derivatives of compounds listed herein to alter melanogenesis. In vivo applications are directed to the administration of at least one of the novel melanogenesis inhibiting compounds listed herein to a subject in need thereof to reduce pigmentation levels for prophylactic, therapeutic and/or cosmetic purposes.

Thus, in one aspect compounds have been identified that are capable of effectively and efficiently inhibiting melanogenesis (referred to herein as melanogenesis inhibitors) in mammalian cells. The ability of such compounds to decrease or inhibit melanogenesis may be used to advantage to decrease the melanin content of melanocytes, which, in turn, results in decreased pigmentation or lightening of skin, hair, wool, or fur color. In view of the above, the novel melanogenesis inhibitors disclosed herein may be topically applied to skin, hair, wool, or fur to lighten their color.

In one embodiment, coumarin compounds are disclosed that are melanogenesis modifiers, such as inhibitors, having a formula (I):

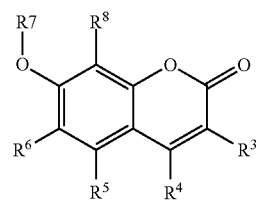

wherein $R^3$ is selected from H, halo, substituted or unsubstituted alkyl, substituted or unsubstituted alkenyl, or substituted or unsubstituted aryl; and substituted or unsubstituted heteroaryl;

$R^4$ is selected from H, halo, hydroxy, alkoxy, alkenyloxy, substituted or unsubstituted alkyl, substituted or unsubstituted alkenyl, and substituted or unsubstituted phenyl;

each $R^5$, $R^6$, and $R^8$ is independently selected from H, halo, hydroxy, alkoxy, alkenyloxy, substituted or unsubstituted alkyl, substituted or unsubstituted alkenyl, and substituted or unsubstituted phenyl;

$R^7$ is selected from H, halo, hydroxy, alkoxy, alkenyloxy, substituted or unsubstituted alkyl, substituted or unsubstituted alkenyl, or heterocycloalkyl; or $R^7$ is —P(=O)(alkoxy)$_2$, or —P(=S)(alkoxy)$_2$; or $R^6$ and $R^7$ or $R^7$ and $R^8$ are joined to form a 5- or 6-membered heterocycloalkyl or heterocycloalkenyl; and the heterocycloalkyl or heterocycloalkenyl is unsubstituted or substituted with one more groups selected from alkyl, alkenyl, hydroxyalkyl, acyloxyalkyl, hydroxy, and alkoxy; and provided that
i) when $R^3$ is H; then $R^8$ is substituted or unsubstituted alkenyl;
ii) the compound is other than robustic acid;
iii) when each of $R^3$, $R^4$, $R^5$, and $R^6$ is H; and $R^8$ is 3-methylbut-2-enyl; then $R^7$ is other than Me;

or pharmaceutically acceptable salts, solvates, isomers, tautomers, metabolites, analogs, isotopic variants or prodrugs thereof.

Another aspect of the invention provides a method for preventing inhibiting melanogenesis or a method for promoting skin lightening comprising administering an effective amount of a compound of formula I.

In one embodiment of the invention, with respect to formula I, $R^7$ is selected from H, substituted or unsubstituted alkyl, and substituted or unsubstituted alkenyl.

In one embodiment of the invention, with respect to formula I, $R^3$ is H, Cl, alkyl, or substituted or unsubstituted phenyl.

In another embodiment of the invention, with respect to formula I, $R^3$ is H, Cl, Me, phenyl, 4-hydroxyphenyl, or 4-methoxyphenyl.

In one embodiment of the invention, with respect to formula I, $R^4$ is H, Cl, alkyl, or substituted or unsubstituted phenyl.

In another embodiment of the invention, with respect to formula I, $R^4$ is H, Cl, Me, phenyl, or 4-methoxyphenyl.

In one embodiment of the invention, with respect to formula I, $R^5$ is H, Cl, alkyl, hydroxy, or alkoxy.

In another embodiment of the invention, with respect to formula I, $R^5$ is H, Cl, Me, OH, or OMe.

In one embodiment of the invention, with respect to formula I, $R^6$ is H, Cl, alkyl, alkenyl, hydroxy, alkoxy, or alkenyloxy.

In another embodiment of the invention, with respect to formula I, $R^6$ is H, Cl, OH, OMe, 3-methylbut-2-enyl, or 3-methylbut-2-enyloxy.

In one particular embodiment of the invention, with respect to formula I, $R^6$ is H, H, or OMe.

In one embodiment of the invention, with respect to formula I, $R^8$ is H, Cl, alkyl, alkenyl, hydroxy, alkoxy, or alkenyloxy.

In another embodiment of the invention, with respect to formula I, $R^8$ is H, Cl, OH, OMe, 3-methylbut-2-enyl, or 3-methylbut-2-enyloxy.

In one particular embodiment of the invention, with respect to formula I, $R^8$ is H, OH, OMe, or 3-methylbut-2-enyl.

In one particular embodiment of the invention, with respect to formula I, $R^7$ is H, Me, 3-methylbut-2-enyl, $P(=O)(OEt)_2$, $P(=S)(OEt)_2$, or 6-hydroxymethyl-3,4,5-trihydroxypyran-2-yl.

In one particular embodiment of the invention, with respect to formula I, each $R^3$, $R^4$, $R^5$, $R^6$ is H; $R^7$ is as described for formula I; and $R^8$ is substituted or unsubstituted alkenyl. In another embodiment, $R^8$ is 3-methylbut-2-enyl, and $R^7$ is other than Me.

In one particular embodiment of the invention, with respect to formula I, each $R^3$, $R^4$, $R^5$, $R^6$ is H; $R^8$ is substituted or unsubstituted alkenyl; and $R^7$ is H, Me, 3-methylbut-2-enyl, $P(=O)(OEt)_2$, $P(=S)(OEt)_2$, or 6-hydroxymethyl-3,4,5-trihydroxypyran-2-yl. In another embodiment, $R^8$ is substituted or unsubstituted alkenyl; and $R^7$ is Me. In yet another particular embodiment, $R^8$ is 3-methylbut-2-enyl and $R^7$ is Me.

In one particular embodiment of the invention, with respect to formula I, $R^4$, $R^5$, $R^6$, $R^7$ and $R^8$ are as described for formula I; and $R^3$ is Cl.

In one particular embodiment of the invention, with respect to formula I, $R^4$, $R^5$, $R^6$, and $R^8$ are as described for formula I; and $R^3$ is Cl; and $R^7$ is H, Me, 3-methylbut-2-enyl, $P(=O)(OEt)_2$, $P(=S)(OEt)_2$, or 6-hydroxymethyl-3,4,5-trihydroxypyran-2-yl. In another embodiment, $R^7$ is Me, or $P(=S)(OEt)_2$. In yet another embodiment, $R^7$ is Me, or $P(=S)(OEt)_2$.

In one particular embodiment of the invention, with respect to formula I, the compound is coumophos.

In one embodiment of the invention, with respect to formula I, $R^6$ and $R^7$ are joined to form a 5- or 6-membered heterocycloalkyl or heterocycloalkenyl; and the heterocycloalkyl or heterocycloalkenyl is unsubstituted or substituted with one more groups selected from alkyl, alkenyl, hydroxyalkyl, acyloxyalkyl, hydroxy, and alkoxy.

In one embodiment of the invention, with respect to formula I, $R^7$ and $R^8$ are joined to form a 5- or 6-membered heterocycloalkyl or heterocycloalkenyl; and the heterocycloalkyl or heterocycloalkenyl is unsubstituted or substituted with one more groups selected from alkyl, alkenyl, hydroxyalkyl, acyloxyalkyl, hydroxy, and alkoxy.

In one embodiment of the invention, with respect to formula I, the compound is according to formulae IIa, IIb, IIc, or IId:

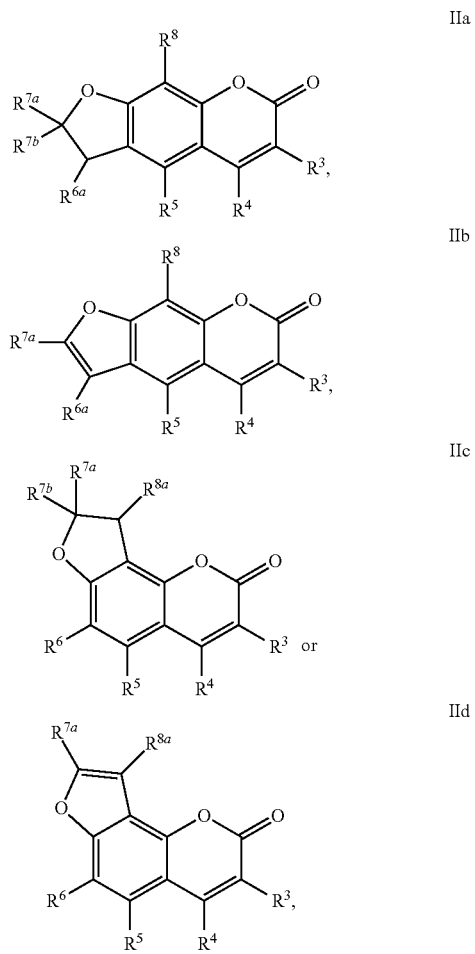

or a pharmaceutically acceptable salt, solvate or prodrug thereof, and stereoisomers, tautomers and isotopic variants thereof; and wherein $R^4$, $R^5$, and $R^6$ are as described for formula I;

$R^3$ is selected from halo, substituted or unsubstituted alkyl, substituted or unsubstituted alkenyl, or substituted or unsubstituted phenyl;

$R^8$ is selected from H, halo, hydroxy, alkoxy, alkenyloxy, substituted or unsubstituted alkyl, substituted or unsubstituted alkenyl, or substituted or unsubstituted phenyl; and each $R^{6a}$, $R^{7a}$, $R^{7b}$, and $R^{8a}$ is independently selected from H, alkyl, hydroxyalkyl, or alkenyl.

In one embodiment of the invention, with respect to formula I, the compound is according to formulae IIIa, IIIb, IIIc or IIId:

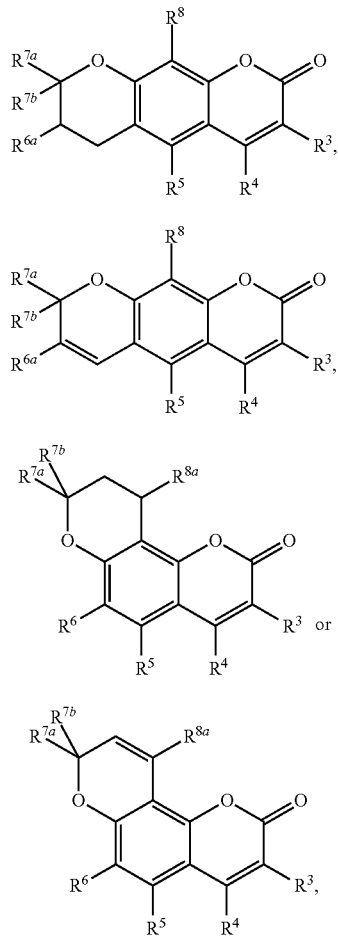

IIIa

IIIb

IIIc

IIId

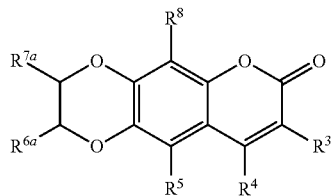

IV or a pharmaceutically acceptable salt, solvate or prodrug thereof, and stereoisomers, tautomers and isotopic variants thereof; and wherein $R^4$, $R^5$, and $R^6$ are as described for formula I;

$R^3$ is selected from halo, substituted or unsubstituted alkyl, substituted or unsubstituted alkenyl, or substituted or unsubstituted phenyl;

$R^8$ is selected from H, halo, hydroxy, alkoxy, alkenyloxy, substituted or unsubstituted alkyl, substituted or unsubstituted alkenyl, or substituted or unsubstituted phenyl; and each $R^{6a}$, $R^{7a}$ and $R^{7b}$ is independently selected from H, alkyl, hydroxyalkyl, or alkenyl.

In one embodiment of the invention, with respect to formulae IIa, IIc, IIIa-IIId, $R^{7a}$ is H or Me.

In one embodiment of the invention, with respect to formulae IIa, IIc, IIIa-IIId, $R^{7b}$ is H or Me.

In one particular embodiment, each of $R^{7a}$ and $R^{7b}$ is Me.

In one embodiment of the invention, with respect to formulae IIc, IId, IIIc, or IIId, $R^{8a}$ is H or Me.

In one embodiment of the invention, with respect to formulae IIc, IId, IIIc, or IIId, $R^6$ is H, Me, OH, OMe, 3-methylbuten-2-yl, or 3-methylbuten-2-yloxy.

In one embodiment of the invention, with respect to formula I, the compound is according to formula IV:

or a pharmaceutically acceptable salt, solvate or prodrug thereof, and stereoisomers, tautomers and isotopic variants thereof; and wherein $R^4$ and $R^5$ are as described for formula I;

$R^3$ is selected from halo, substituted or unsubstituted alkyl, substituted or unsubstituted alkenyl, or substituted or unsubstituted phenyl;

$R^8$ is selected from H, halo, hydroxy, alkoxy, alkenyloxy, substituted or unsubstituted alkyl, substituted or unsubstituted alkenyl, or substituted or unsubstituted phenyl; and each $R^{6a}$ and $R^{7a}$ is independently selected from H, alkyl, or alkenyl.

In one embodiment of the invention, with respect to formulae I-IV, $R^4$ is H, Cl, alkyl, hydroxy, alkoxy, or substituted or unsubstituted phenyl.

In one embodiment of the invention, with respect to formulae I-IV, $R^4$ is H, Me, OH, OMe, or 4-methoxyphenyl.

In one embodiment of the invention, with respect to formulae I-IV, $R^4$ is OH or OMe.

In one embodiment of the invention, with respect to formulae I-IV, $R^{6a}$ is H or Me.

In one embodiment of the invention, with respect to formulae I-IV, $R^{6a}$ is H.

In one embodiment of the invention, with respect to formulae I-IV, $R^{7a}$ is H or Me.

In one embodiment of the invention, with respect to formulae I-IV, $R^{7b}$ is H or Me.

In one embodiment of the invention, with respect to formulae I-IV, each $R^{7a}$ and $R^{7b}$ is H or Me.

In one embodiment of the invention, with respect to formulae I-IV, each $R^{7a}$ and $R^{7b}$ is Me.

In one embodiment of the invention, with respect to formulae I-IV, $R^{8a}$ is H or Me.

In one embodiment of the invention, with respect to formula I, the compound is of formula Va, Vb, Vc, or Vd:

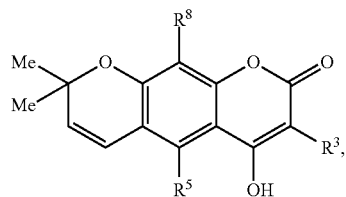

Va

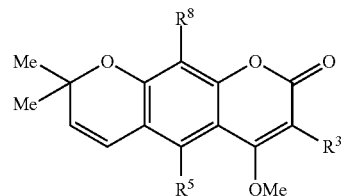

Vb

-continued

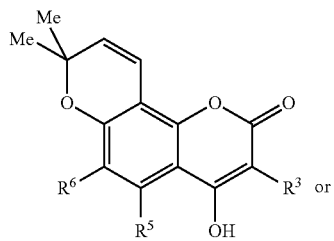
Vc

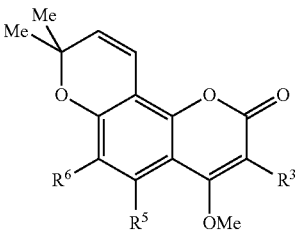
Vd or a pharmaceutically acceptable salt, solvate or prodrug thereof, and stereoisomers, tautomers and isotopic variants thereof; and wherein $R^4$, $R^5$, and $R^6$ are as in formula I;

$R^3$ is selected from halo, substituted or unsubstituted alkyl, substituted or unsubstituted alkenyl, or substituted or unsubstituted phenyl; and $R^8$ is selected from H, halo, hydroxy, alkoxy, alkenyloxy, substituted or unsubstituted alkyl, substituted or unsubstituted alkenyl, or substituted or unsubstituted phenyl.

In one embodiment of the invention, with respect to formulae I-Vd, $R^5$ is H, Cl, alkyl, hydroxy, or alkoxy.

In one embodiment of the invention, with respect to formulae I-Vd, $R^5$ is H, Cl, Me, OH, or OMe.

In one embodiment of the invention, with respect to formulae I-Vd, $R^5$ is OH or OMe.

In one embodiment of the invention, with respect to formulae I-Vd, $R^8$ is H, Cl, alkyl, alkenyl, hydroxy, alkoxy, or alkenyloxy.

In one embodiment of the invention, with respect to formulae I-Vd, $R^8$ is H, Cl, OH, OMe, 3-methylbut-2-enyl, or 3-methylbut-2-enyloxy.

In one embodiment of the invention, with respect to formulae I-Vd, $R^8$ is H or 3-methylbut-2-enyl.

In one embodiment of the invention, with respect to formulae I-Vd, $R^6$ is H, Cl, alkyl, alkenyl, hydroxy, alkoxy, or alkenyloxy.

In one embodiment of the invention, with respect to formulae I-Vd, $R^6$ is H, Cl, OH, OMe, 3-methylbut-2-enyl, or 3-methylbut-2-enyloxy.

In one embodiment of the invention, with respect to formulae I-Vd, $R^6$ is 3-methylbut-2-enyl.

In one embodiment of the invention, with respect to formula I, the compound is of formula VIa, VIb, VIc, or VId:

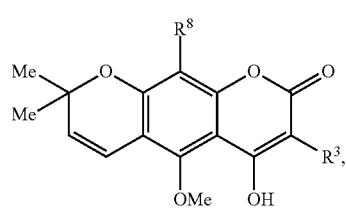
VIa

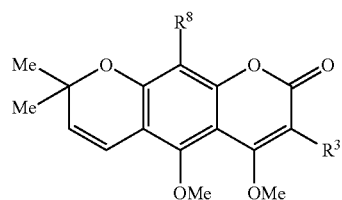
VIb

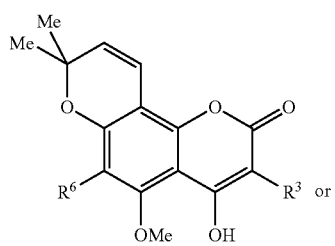
VIc

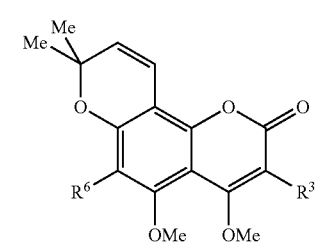
VId or a pharmaceutically acceptable salt, solvate or prodrug thereof, and stereoisomers, tautomers and isotopic variants thereof; and wherein $R^3$ is selected from halo, substituted or unsubstituted alkyl, substituted or unsubstituted alkenyl, or substituted or unsubstituted phenyl.

In one embodiment of the invention, with respect to formulae I-VId, $R^3$ is Cl, alkyl, or substituted or unsubstituted phenyl.

In one embodiment of the invention, with respect to formulae I-VId, $R^3$ is Me, phenyl, 4-hydroxyphenyl, 3,4-dihydroxyphenyl, 4-methoxyphenyl, or 3,4-dimethoxyphenyl.

In one embodiment of the invention, with respect to formula I, the compound is of formula VIIa or VIIb:

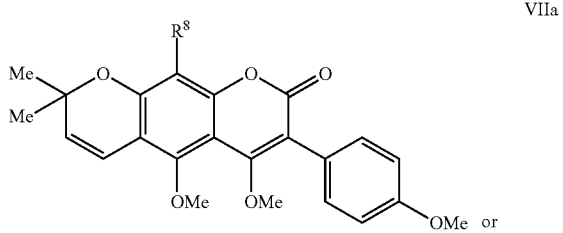
VIIa or

-continued

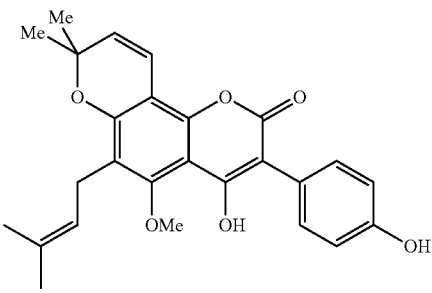
VIIb or a pharmaceutically acceptable salt, solvate or prodrug thereof, and stereoisomers, tautomers and isotopic variants thereof.

In one embodiment of the invention, with respect to formula I, the compound is pachyrrhizin, robustic acid methyl ether, or scandenin.

In one embodiment of the invention, with respect to formula I, the compound is robustic acid methyl ether.

In one embodiment of the invention, with respect to formula I, the compound is scandenin.

In one embodiment of the invention, with respect to formula I, the compound is pachyrrhizin.

In one particular embodiment, with respect to formula I, the compound is formula VIIa (robustic acid methyl ether):

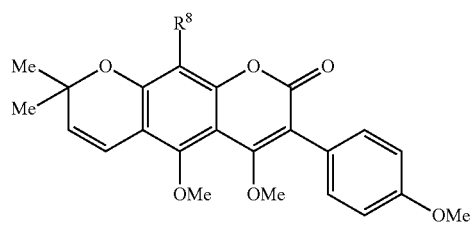
VIIa or pharmaceutically acceptable salts, solvates, isomers, tautomers, metabolites, analogs, isotopic variants or prodrugs thereof.

In another particular embodiment, with respect to formula I, the compound is formula VIIb (scandenin):

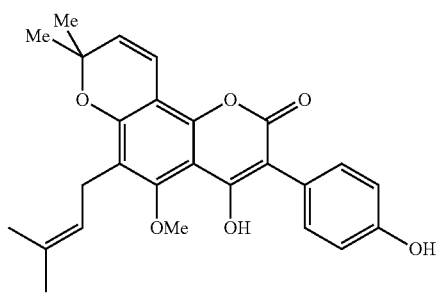
VIIb or pharmaceutically acceptable salts, solvates, isomers, tautomers, metabolites, analogs, isotopic variants or prodrugs thereof.

In another particular embodiment, with respect to formula I, the compound is selected from the compounds listed in Table 1.

In another aspect, the invention provides methods for inhibiting melanogenesis using the compounds of formulae I-VIIb.

In another aspect, the invention provides methods for inhibiting melanogenesis using a plant extract containing compounds of formula I. In one embodiment the plant extract is derived from *Derris scandens*.

In another aspect, the invention provides methods for promoting skin lightening using the compounds of formulae I-VIIb.

In another aspect, the invention provides methods for promoting skin lightening using a plant extract containing compounds of formula I. In one embodiment the plant extract is derived from *derris scandens*. In one particular embodiment, the *Derris scandens* extract is prepared by an ethanol extraction method.

A further aspect extends to a formulation that comprises a combination of a compound with respect to formulae I-VIIb, and an additional pharmaceutical or cosmetic agent. In one embodiment, the additional pharmaceutical or cosmetic agent is a like-acting agent. In a particular embodiment, the like acting agent is selected from a cosmetic ingredient and a pharmacologically active agent.

In one embodiment of the combination just described, a pharmaceutical composition is prepared that is useful to treat a disease for which a melanogenesis inhibitor is indicated, which comprises a therapeutically effective amount of the combination, wherein the like acting agent is a pharmacologically active agent. More particularly, the like-acting agent is a skin lightening or skin bleaching compound. In some embodiments, the skin lightening or skin bleaching compound is hydroquinone, kojic acid, ascorbic acid, magnesium ascorbyl phosphate or ascorbyl glucosamine, or mixtures thereof In a further embodiment of the combination described above, a topical formulation is prepared that comprises a composition for cosmetic or dermatological use, which composition comprises a cosmetically and/or dermatologically effective amount of the combination stated above, wherein the like acting agent is a cosmetically active agent. More particularly, the like-acting agent is a skin lightening or skin bleaching compound. In some embodiments, the skin lightening or skin bleaching compound is hydroquinone, kojic acid, ascorbic acid, magnesium ascorbyl phosphate or ascorbyl glucosamine, or mixtures thereof.

In another embodiment of the combination described above, the additional pharmaceutical or cosmetic agent is a skin care active agent. In some embodiments, the skin care active agent is an abrasive, an absorbent, an astringent, an aesthetic component, such as fragrances, pigments, colorings/colorants, essential oils, skin sensates, astringents and other aesthetic components, an antioxidant, a reducing agent, a sequestrant, a skin bleaching or lightening agent, a skin conditioning agent, for example humectants and emollients, a skin soothing agent, a skin healing agent, such as pathenol and derivatives, aloe vera, pantothenic acid, allantoin, bisbolol, dipotassium glycyrrhizinate, skin treating agents, vitamins and derivatives, such as a retinoid, or mixtures thereof. In some embodiments, the retinoid is retinol, retinal, retinol esters, retinyl propionate, retinoic acid, retinyl palmitate, or mixtures thereof.

In a further aspect, also provided are methods for preventing, treating, ameliorating or managing a disease or condition involving undesired or aberrant melanogenesis, which comprises administering to a patient in need or desirous of such prevention, treatment, amelioration or management, a pharmaceutical composition comprising a prophylactically or therapeutically effective melanogenesis-inhibiting amount of the combination as stated and set forth above, wherein the like acting agent is a pharmaceutically active agent. More particularly, the like-acting agent is a skin lightening or skin bleaching compound. In some embodiments, the skin lightening or skin bleaching compound is hydroquinone, kojic acid, ascorbic acid, magnesium ascorbyl phosphate or ascorbyl glucosamine, or mixtures thereof.

A method for altering or restoring pigmentation in mammalian skin, hair, wool or fur comprising administering to the mammalian skin, hair, wool or fur an amount of a composition comprising a pigment restoring or altering-effective amount of the combination as stated and set forth above, wherein the like acting agent is a cosmetically active agent. More particularly, the like-acting agent is a skin lightening or skin bleaching compound. In some embodiments, the skin lightening or skin bleaching compound is hydroquinone, kojic acid, ascorbic acid, magnesium ascorbyl phosphate or ascorbyl glucosamine, or mixtures thereof.

The methods and compositions disclosed herein contemplate the use of one or more of the compounds listed herein as an active ingredient(s) for various uses. In a particular embodiment, the active ingredient(s) is combined with an acceptable carrier to form a topical formulation for application to the skin, for example, for cosmetic and/or therapeutic dermatological uses. Topical formulations may include ointments, lotions, pastes, creams, gels, drops, suppositories, sprays, liquids, shampoos, powders, antiperspirants, deodorants, rinses, soaps, topical make-up products, including but not limited to face power, foundation, rouge, eye shadow, mascara, eyeliner or lipstick, UV-protective products, which may include sunscreens, lotions or creams, and transdermal patches. Thickeners, diluents, emulsifiers, dispersing aids or binders may be used as needed. Preferably, one function of the carrier is to enhance skin penetration of the active ingredient(s), and should be capable of delivering the active ingredient(s) to melanocytes under in vivo conditions. Suitable carriers are well known to skilled practitioners, and include liposomes, ethanol, dimethylsulfoxide (DMSO), petroleum jelly (petrolatum), mineral oil (liquid petrolatum), water, dimethylformamide, dekaoxyethylene-oleylether, oleic acid, 2-pyrrolidone and Azone® brand penetration enhancer (Upjohn). A particular composition may be formulated to include an active ingredient(s) as described in Table I, with one of 2-pyrrolidone, oleic acid and/or Azone® added to enhance penetration, solubilized in a base of water, ethanol, propanol and/or propylene glycol.

As indicated above, vehicles comprising liposomes may be used for topical delivery of some of the compositions disclosed herein. Depending on the composition, and at the discretion of a skilled practitioner, such liposomes may be non-ionic and contain a) glycerol dilaurate (preferably in an amount of between about 5% and about 70% by weight); b) compounds having the coumarin core found in cholesterol (preferably in an amount of between about 5% and about 45% by weight); and c) one or more fatty acid ethers having from about 12 to about 18 carbon atoms preferably in an amount of between about 5% and about 70% by weight collectively), wherein the constituent compounds of the liposomes are preferably in a ratio of about 37.5:12.5:33.3:16.7. For some compositions, liposomes comprised of glycerol dilaurate/cholesterol/polyoxyethylene-10-stearyl ether/polyoxyethylene-9-lauryl ether (GDL liposomes) are preferred. Liposomes may be present in an amount, based upon the total volume of the composition, of from about 10 mg/mL to about 100 mg/mL, and more preferably from about 20 mg/mL to about 50 mg/mL. A ratio of about 37.5:12.5:33.3:16.7 may be used to particular advantage. Suitable liposomes may be prepared in accordance with standard methods commonly used in the art.

The above described composition may be prepared by combining the desired components in a suitable container and mixing them under ambient conditions in any conventional high shear mixing means well known in the art for non-ionic liposome preparations, such as those disclosed in Niemiec et al. (Pharm. Res. 12:1184-88 (1995)), which is incorporated by reference herein in its entirety. The presence of such liposomes enhances the depigmenting capabilities of some compositions.

Other formulations may contain, for example, soybean milk or other liquid formulations derived directly from legumes or other suitable plant. Such a formulation may, for example, contain a large proportion of soybean milk, an emulsifier that maintains the physical stability of the soybean milk, and, optionally a chelating agent, preservatives, emollients, humectants and/or thickeners or gelling agents.

Oil-in-water emulsions, water-in-oil emulsions, solvent-based formulations and aqueous gels known to those of skill in the art may also be utilized as vehicles for the delivery of the disclosed compositions.

Depending on the specific application, the compositions disclosed herein may also include other active ingredients, as well as inert or inactive ingredients. In such alternative embodiments, the topically active pharmaceutical or cosmetic composition may be optionally combined with other ingredients such as moisturizers, cosmetic adjuvants, surfactants, foaming agents, conditioners, humectants, fragrances, viscosifiers, buffering agents, preservatives, sunscreens and the like.

Particular formulations may include at least one active ingredient (for example, a novel melanogenesis modifier described herein) or previously recognized, and particularly, like-acting agents, such as skin lighteners or skin bleachers, which may be known to those of skill in the art. Agents known to possess similar activities and/or properties include, but are not limited to: bleaching agents; tyrosinase inhibitors; α-hydroxy acids, salts and derivatives thereof; α-keto acids, salts and derivatives thereof; β-hydroxy acids, salts and derivatives thereof; retinoids, salts and derivatives thereof; Vitamin A and related compounds; acids; phenol; methoxypropyl-gluconamide; corticosteroids; agents that block the transfer of melanosomes to keratinocytes, such as may be found in soy extracts; kojic acid; licorice extracts; and the like. In some embodiments, the retinoids include retinol, retinal, retinol esters, retinyl propionate, retinoic acid, retinyl palmitate or mixtures thereof.

The dose regimen will depend on a number of factors which may readily be determined, such as severity and responsiveness of the condition to be treated, but will normally be one or more doses per day, with a course of treatment lasting from several days to several months, or until a cure is effected or a diminution of disease state is achieved, or a cosmetically desired degree of melanogenesis modification (e.g., reduction in pigmentation) is achieved, depending on the application. One of ordinary skill may readily determine optimum dosages, dosing methodologies and repetition rates. In general, it is contemplated that the compositions disclosed herein will have a concentration of a melanogenesis inhibitor of from about 0.01% to about 50%, preferably from about 0.03% to about 10%. In some embodiments, the compositions disclosed herein will have a concentration of melanogenesis inhibitor of from about 0.1% to about 25%, or from about 1% to about 10%. In other embodiments, the compositions disclosed herein will have a concentration of from about 0.1% to about 75%, from about 0.5% to about 60%, from about 0.5% to about 50%, from about 0.5% to about 40%, from about 0.5% to about 30%, from about 0.5% to about 20%, from about 0.5% to about 10%, from about 1% to about 75%, from about 1% to about 60%, from about 1% to about 50%, from about 1% to about 40%, from about 1% to about 30%, from about 1% to about 20%, from about 1% to about 10%, from about 5% to about 75%, from about 5% to about 60%, from about 5% to about 50%, from about 5% to about 40%, from about 5% to about 30%, from about 5% to about 20%, from about 5% to about 10%, from about 10% to about 75%, from about 10% to about 60%, from about 10% to about 50%, from about 10% to about 40%, from about 10% to about 30%, from about 10% to about 20%, and from about 10% to about 15%. In some embodiments, the compositions disclosed herein will have a concentration of melanogenesis inhibitor of 0.1%, 0.5%, 0.75%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 10.5%, 11%, 11.5%, 12%, 12.5%, 13%, 13.5%, 14%, 14.5%, 15%, 16%, 17%, 18%, 19%, 20%, 25%, 30%, 35% 40%, 45% or 50%.

It is also contemplated that the compositions disclosed herein may contain from about 0.01 mg to about 100 mg of melanogenesis inhibitor, preferably about 0.1 mg to about 10 mg of melanogenesis inhibitor. In some embodiments, the compositions disclosed herein may contain from about 0.05 to about 5 mg of melanogenesis inhibitor, or from about 0.1 to about 3 mg of melanogenesis inhibitor. In some embodiments, the compositions disclosed herein may contain from about 0.1 to about 50 mg, from about 0.1 to about 45 mg, from about 0.1 to about 40 mg, from about 0.1 to about 35 mg, from about 0.1 to about 30 mg, from about 0.1 to about 25 mg, from about 0.1 to about 20 mg, from about 0.1 to about 15 mg, from about 0.1 to about 10 mg, from about 0.1 to about 5 mg, from about 0.5 to about 50 mg, from about 0.5 to about 45 mg, from about 0.5 to about 40 mg, from about 0.5 to about 35 mg, from about 0.5 to about 30 mg, from about 0.5 to about 25 mg, from about 0.5 to about 20 mg, from about 0.5 to about 15 mg, from about 0.5 to about 10 mg, from about 0.5 to about 5 mg, from about 1.0 to about 50 mg, from about 1.0 to about 45 mg, from about 1.0 to about 40 mg, from about 1.0 to about 35 mg, from about 1.0 to about 30 mg, from about 1.0 to about 25 mg, from about 1.0 to about 20 mg, from about 1.0 to about 15 mg, from about 1.0 to about 10 mg, from about 1.0 to about 5 mg, from about 2.5 to about 50 mg, from about 2.5 to about 45 mg, from about 2.5 to about 40 mg, from about 2.5 to about 35 mg, from about 2.5 to about 30 mg, from about 2.5 to about 25 mg, from about 2.5 to about 20 mg, from about 2.5 to about 15 mg, from about 2.5 to about 10 mg, and from about 2.5 to about 5 mg. In some embodiments, the compositions disclosed herein will contain from about 0.1 mg, 0.2 mg, 0.3 mg, 0.4 mg, 0.5, mg, 0.6 mg, 0.7 mg, 0.8 mg, 0.9 mg, 1.0 mg, 2.0 mg, 3.0 mg, 4.0 mg, 5.0 mg, 7.0 mg, 10.0 mg, 15.0 mg, 20 mg, 25 mg, 30 mg, 35 mg, 40 mg, 45 mg, 50 mg, 60 mg, 70 mg, 80 mg, 90 mg or 100 mg of melanogenesis inhibitor. In some embodiments, the compositions disclosed herein will contain from about 0.3 mg to about 0.75 mg of melanogenesis inhibitor.

It is further contemplated that the compositions disclosed herein will have a concentration of melanogenesis inhibitor of from about 0.01 mg/ml to about 50 mg/ml, preferably from about 0.1 mg/ml to about 10 mg/ml. In some embodiments, the compositions disclosed herein will have a concentration of melanogenesis inhibitor of from about 0.1 mg/ml to about 5 mg/ml, or from about 0.3 mg/ml to about 3 mg/ml. In some embodiments, the compositions will have a concentration of melanogenesis inhibitor of from about 0.1 to about 50 mg/ml, from about 0.1 to about 45 mg/ml, from about 0.1 to about 40 mg/ml, from about 0.1 to about 35 mg/ml, from about 0.1 to about 30 mg/ml, from about 0.1 to about 25 mg/ml, from about 0.1 to about 20 mg/ml, from about 0.1 to about 15 mg/ml, from about 0.1 to about 10 mg/ml, from about 0.1 to about 5 mg/ml, 0.5 to about 50 mg/ml, from about 0.5 to about 45 mg/ml, from about 0.5 to about 40 mg/ml, from about 0.5 to about 35 mg/ml, from about 0.5 to about 30 mg/ml, from about 0.5 to about 25 mg/ml, from about 0.5 to about 20 mg/ml, from about 0.5 to about 15 mg/ml, from about 0.5 to about 10 mg/ml, from about 0.5 to about 5 mg/ml, 1.0 to about 50 mg/ml, from about 1.0 to about 45 mg/ml, from about 1.0 to about 40 mg/ml, from about 1.0 to about 35 mg/ml, from about 1.0 to about 30 mg/ml, from about 1.0 to about 25 mg/ml, from about 1.0 to about 20 mg/ml, from about 1.0 to about 15 mg/ml, from about 1.0 to about 10 mg/ml, from about 1.0 to about 5 mg/ml, 2.5 to about 50 mg/ml, from about 2.5 to about 45 mg/ml, from about 2.5 to about 40 mg/ml, from about 2.5 to about 35 mg/ml, from about 2.5 to about 30 mg/ml, from about 2.5 to about 25 mg/ml, from about 2.5 to about 20 mg/ml, from about 2.5 to about 15 mg/ml, from about 2.5 to about 10 mg/ml, from about 2.5 to about 5 mg/ml. In some embodiments, the compositions disclosed herein will have a concentration of melanogenesis inhibitor of 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11, 11.5, 12, 12.5, 13, 13.5, 14, 14.5, 15, 16, 17, 18, 19, 20, 25, 30, 35 40, 45 or 50 mg/ml.

In general, melanogenesis inhibitors or compounds that decrease or suppress melanin production and pigmentation in mammalian skin, hair, fur or wool are useful in, for example, the lightening and/or brightening of skin, hair, wool or fur for cosmetic purposes, or the treatment of hyperpigmentation or uneven pigmentation disorders such as vitiligo, ephelides, lentigines, dermal melanocytosis, cafe-au-lait spots, post-inflammatory hyperpigmentation, etc. For such depigmentation applications, the formulation and dosing would be as described above.

In certain aspects, prodrugs and derivatives of the disclosed compounds are provided. Prodrugs are derivatives of the compounds which have metabolically cleavable groups and become by solvolysis or under physiological conditions the compounds which are pharmaceutically active, in vivo. Such examples include, but are not limited to, choline ester derivatives and the like, N-alkylmorpholine esters and the like.

Other derivatives of the compounds have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the disclosed compounds are preferred prodrugs. In some cases it is desirable to prepare double ester type prodrugs such as (acyloxy)alkyl esters or ((alkoxycarbonyl)oxy)alkylesters. Preferred are the substituted or unsubstituted $C_1$ to $C_8$ alkyl, substituted or unsubstituted $C_2$-$C_8$ alkenyl, aryl, substituted or unsubstituted $C_7$-$C_{12}$ aryl, and substituted or unsubstituted $C_7$-$C_{12}$ arylalkyl esters of the compounds.

Also included are pharmaceutically acceptable acid addition and base salts of any of the aforementioned compounds of formulae I-VIIb. The acids which are used to prepare the pharmaceutically acceptable acid addition salts of the aforementioned base compounds are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1-methylene-bis-(2-hydroxy-3-naphthoate)) salts.

The compounds useful that are basic in nature are capable of forming a wide variety of different salts with various inorganic and organic acids. Although such salts must be pharmaceutically acceptable for administration to animals, it is often desirable in practice to initially isolate a compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds disclosed herein are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds useful that are acidic in nature are capable of forming base salts with various pharmaceutically acceptable cations. Examples of such salts include the alkali metal and alkaline earth metal salts and, particularly, the sodium and potassium salts. These salts can be prepared by conventional techniques. The chemical bases that are used as reagents to prepare the pharmaceutically acceptable base salts of the compounds disclosed herein are those that form non-toxic base salts with the acidic compounds of formulae I-VIIb. Such non-toxic base salts include those derived from such pharmaceutically acceptable cations as sodium, potassium, calcium and magnesium, etc. These salts can easily be prepared by treating the corresponding acidic compounds with an aqueous solution containing the desired pharmaceutically acceptable cations, and then evaporating the resulting solution to dryness, preferably under reduced pressure. Alternatively, they can also be prepared by mixing lower alkanolic solutions of the acidic compounds and the desired alkali metal alkoxide together, and then evaporating the resulting solution to dryness, as described above. In either case, stoichiometric quantities of reagents are preferably employed in order to ensure completeness of reaction and maximum yields of the desired final products.

The compounds and their pharmaceutically acceptable salts are useful in the treatment of disorders of human pigmentation, including solar and simple lentigines (including age/liver spots), melasma/chloasma and post inflammatory hyper-pigmentation. Such compounds reduce skin melanin levels by inhibiting the production of melanin, whether the latter is produced constitutively or in response to UV irradiation (such as sun exposure). Thus, some of the active compounds used can be used to reduce skin melanin content in non-pathological states so as to induce a lighter skin tone, as desired by the user, or to prevent melanin accumulation in skin that has been exposed to UV irradiation. They can also be used in combination with skin peeling agents (including glycolic acid or trichloroacetic acid face peels) to lighten skin tone and prevent repigmentation.

The appropriate dose regimen, the amount of each dose administered, and specific intervals between doses of the active compound will depend upon the particular active compound employed, the condition of the patient being treated, and the nature and severity of the disorder or condition being treated. Preferably, the melanogenesis inhibitor is administered in an amount and at an interval that results in the desired treatment of or improvement in the disorder or condition being treated.

For skin lightening, a melanogenesis inhibitor disclosed herein can also be used in combination with sun screens (UVA or UVB blockers) to prevent repigmentation, to protect against sun or UV-induced skin darkening or to enhance their ability to reduce skin melanin and their skin bleaching action. For skin lightening, a melanogenesis inhibitor can also be used in combination with retinoic acid or its derivatives or any compounds that interact with retinoic acid receptors and accelerate or enhance the ability to reduce skin melanin and skin bleaching action, or enhance the ability to prevent the accumulation of skin melanin. For skin lightening, a melanogenesis inhibitor can also be used in combination with 4-hydroxyanisole. For skin lightening, the melanogenesis inhibitor can also be used in combination with ascorbic acid, its derivatives and ascorbic-acid based products (such as magnesium ascorbate) or other products with an anti-oxidant mechanism (such as resveratrol or vitamin A or retinoic acid) which accelerate or enhance their ability to reduce skin melanin and their skin bleaching action.

Also provided are compounds useful to decrease melanin production or to reduce skin pigmentation, which correspond to compounds of the formulae I-VIIb, and prodrugs, and analogs thereof, and to pharmaceutical compositions containing them, and including any pharmaceutically acceptable salts or solvates thereof.

Although methods and materials similar or equivalent to those described herein can be used in the practice or testing of the compositions and compounds disclosed herein, preferred methods and materials are described below. The materials, methods, and examples are illustrative only and not intended to be limiting. Other features and advantages will be apparent from the detailed description, examples, and the claims.

Plant Extract Containing Coumarins of Formula I

In some embodiments are methods of inhibiting melanogenesis comprising administering to melanocytes an effective amount of a plant extract containing a melanogenesis inhibitor. In some embodiments, the melanogenesis inhibitor is a coumarin melanogenesis inhibitor as in Formula I. In some embodiments, the melanogenesis inhibitor is scandenin or a scandenin derivative. In some embodiments, the plant extract is derived from a plant of the Derris family. In some embodiments, the plant extract is extract derived from *Derris scandens*. The plant species listed are not meant to be limiting as to the source of the melanogenesis inhibitor. Other plant species through which plant extracts can be made comprising a melanogenesis inhibitor, including a scandenin or a scandenin derivative, may also be used in conjunction with the disclosure herein.

In some embodiments, the plant extract is substantially purified or partially purified for concentration of the melanogenesis inhibitor. In yet other embodiments, the plant extract may be substantially liquefied or partially liquefied for administration to a patient in need thereof. The plant extract may also be processed to remove particulate matter prior to administration. In some embodiments, the plant extract contains about 0.1 to about 90%, about 0.5% to about 80%, about 1% to about 75%, about 5% to about 60%, about 10% to about 50%, about 25% to about 40% melanogenesis inhibitor. In other embodiments, the plant extract contains about 1% to about 80%, about 1% to about 70%, about 1% to about 60%, about 1% to about 50%, about 1% to about 40%, about 1% to about 30%, about 1% to about 20%, about 1% to about 10%, about 5% to about 80%, about 5% to about 70%, about 5% to about 60%, about 5% to about 50%, about 5% to about 40%, about 5% to about 30%, about 5% to about 20%, about 5% to about 10%, about 10% to about 80%, about 10% to about 70%, about 10% to about 60%, about 10% to about 50%, about 10% to about 40%, about 10% to about 30% or about 10% to about 20% melanogenesis inhibitor. In some embodiments, the plant extract contains about 0.5%, 1%, 5%, 10%, 15%, 20%, 25%, 30%, 35%, 40%, 45%, 50%, 55%, 60%, 65%, 70%, 75%, 80%, 85%, 90%, or 95% of a melanogenesis inhibitor.

In some embodiments, a plant extract is provided containing scandenin or a scandenin derivative for use as an inhibitor of melanogenesis. In some embodiments, provided are formulations of a plant extract containing scandenin or a scandenin derivative for inhibiting melanogenesis. Also provided are methods for preventing, treating, ameliorating or managing a disease or condition involving undesired or aberrant melanogenesis, which comprises administering to a patient in need thereof or desirous of such prevention, treatment, amelioration, or management, a prophylactically, therapeutically or cosmetically effective melanogenesis-inhibiting amount of a plant extract containing scandenin or a scandenin derivative. In some embodiments, provided are methods for altering or restoring pigmentation in mammalian skin, hair, wool, or fur comprising administering to a mammalian skin, hair, wool or fur an effective amount of a plant extract containing scandenin or a scandenin derivative. One example of such plant extract is extract derived from *derris scandens*.

*Derris scandens* powder is commercially available and can be purchased from, for example, KhaoLaor Laboratories, Thailand. *Derris scandens* extract can be prepared from *Derris scandens* powder. In a representative preparation of the plant extract, 5 grams of *Derris scandens* Benth extract powder was brought to 25 ml with 200 proof ethanol, and incubated overnight at room temperature on an agitator. The mixture was then centrifuged twice at 1000 rpm for 10 min in a swing rotor, and then an additional 5 min as above. The supernatant was then filtered through Whatman Grade 1 (11 micron) filter paper. The clarified fluid was then further allowed to settle for an hour, and the supernatant was removed and used as the ethanolic extract of *Derris scandens* Benth.

Extract derived from *Derris scandens* is a potent inhibitor of melanin synthesis in cultured melanocytes and an effective depigmenting agent in human skin tissues. In general, it is contemplated that the plant extract compositions disclosed herein will comprise plant extract of from about 1% to about 75%, preferably from about 5% to about 50%, more preferably from about 10% to about 30%, and more preferably about 20%. In some embodiments, the compositions disclosed herein will have an amount of plant extract of from about 5% to about 35%, or from about 15% to about 25%. In some embodiments, the compositions disclosed herein will have an amount of plant extract of from about 5% to about 75%, from about 5% to about 70%, from about 5% to about 65%, from about 5% to about 60%, from about 5% to about 55%, from about 5% to about 50%, from about 5% to about 45%, from about 5% to about 40%, from about 5% to about 35%, from about 5% to about 30%, from about 5% to about 25%, from about 5% to about 20%, from about 5% to about 15%, from about 5% to about 10%, from about 10% to about 75%, from about 10% to about 70%, from about 10% to about 65%, from about 10% to about 60%, from about 10% to about 55%, from about 10% to about 50%, from about 10% to about 45%, from about 10% to about 40%, from about 10% to about 35%, from about 10% to about 30%, from about 10% to about 25%, from about 10% to about 20%, and from about 10% to about 15%. In some embodiments, the compositions disclosed herein will have an amount of plant extract of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 32%, 34%, 35%, 36%, 38%, 40%, 45%, 50%, 55%, 60%, 65%, 70% or 75%. The amount of plant extract included in the disclosed compositions will depend on a number of factors, including the amount of melanogenesis inhibitor, including scandenin or a scandenin derivative, contained in the plant extract preparation. Testing of the plant extract preparations to determine the amount of melanogenesis inhibitor included in each preparation is contemplated within the scope of the embodiments described herein.

It is also contemplated that the compositions disclosed herein may contain from about 10 mg to about 100 g of plant extract per 100 ml of composition, preferably about 1 g to about 50 g of plant extract per 100 ml of composition. In some embodiments, the compositions disclosed herein may contain from about 100 mg to about 50 g of plant extract per 100 ml of composition, or from about 1 g to about 20 g of plant extract per 100 ml of composition. In some embodiments, the compositions disclosed herein may contain from about 100 mg to about 50 g, from about 100 mg to about 45 g, from about 100 mg to about 40 g, from about 100 mg to about 35 g, from about 100 mg to about 30 g, from about 100 mg to about 25 g, from about 100 mg to about 20 g, from about 100 mg to about 15 g, from about 100 mg to about 10 g, from about 100 mg to about 5 g, from about 100 mg to about 1 g, 1 g to about 50 g, from about 1 g to about 45 g, from about 1 g to about 40 g, from about 1 g to about 35 g, from about 1 g to about 30 g, from about 1 g to about 25 g, from about 1 g to about 20 g, from about 1 g to about 15 g, from about 1 g to about 10 g, from about 1 g to about 5 g, from about 2.5 g to about 50 g, from about 2.5 g to about 45 g, from about 2.5 g to about 40 g, from about 2.5 g to about 35 g, from about 2.5 g to about 30 g, from about 2.5 g to about 25 g, from about 2.5 g to about 20 g, from about 2.5 g to about 15 g, from about 2.5 g to about 10 g, and from about 2.5 g to about 5 g of plant extract per 100 ml of composition. In some embodiments, the compositions disclosed herein will contain from about 0.5 g, 1 g, 2 g, 3 g, 4 g, 5 g, 6 g, 7 g, 8 g, 9 g, 10 g, 11 g, 12 g, 13 g, 14 g, 15 g, 16 g, 17 g, 18 g, 19 g, 20 g, 21 g, 22 g, 23 g, 24 g, 25 g, 26 g, 27 g, 28 g, 29 g, 30 g, 32 g, 35 g, 37 g, 40 g, 45 g, 50 g, 55 g, 60 g, 65 g, 70 g or 75 g of plant extract per 100 ml of composition.

In other embodiments, provided are combinations of a plant extract containing scandenin or a scandenin derivative and a like-acting agent, or robustic acid methyl ether (methyl robustate), or a derivative thereof, and a like-acting agent. One example of such plant extract is extract derived from *Derris scandens*. The like-acting agent can be any cosmetic ingredient or a pharmacologically active agent disclosed herein. Also provided are pharmaceutical compositions useful in treating disease for which a melanogenesis inhibitor is indicated, comprising a therapeutically effective amount of a plant extract containing scandenin or a scandenin derivative in combination with a like-acting agent. In some embodiments, the pharmaceutical composition comprising a plant extract containing scandenin or a scandenin derivative in combination with a like-acting agent is a topical formulation for cosmetic or dermatological use. In still other embodiments, methods are provided for preventing, treating, ameliorating or managing a disease or condition involving undesired or aberrant melanogenesis, which comprises administering to a patient in need thereof or desirous of such prevention, treatment, amelioration or management, a pharmaceutical or cosmetic composition comprising prophylactically, therapeutically or cosmetically effective melanogenesis-inhibiting amount of a combination of a plant extract containing scandenin or a scandenin derivative with a like-acting agent. In still other embodiments, also provided are methods for altering or restoring pigmentation in mammalian skin, hair, wool or fur comprising administering to a mammalian skin, hair, wool or fur an amount of a composition comprising a pigment-restoring or altering-effective amount of a combination of a plant extract containing scandenin or a scandenin derivative with a like-acting agent. In some embodiments, the like-acting agent is a skin lightening compound.

Methods of Inhibiting Melanogenesis

As stated above, the compounds disclosed herein can be used to treat animals or, preferably, humans that have diseases, conditions, or disorders caused by the production or overproduction of melanin. Such diseases, conditions, or disorders include those that can be characterized by discolorations of the skin or hair such as, for example, hyperpigmentation caused by inflammation or from diseases such as melasma, or brown spots such as "cafe au lait" macules. Alternatively, a subject may wish to lighten the color of his or her hair or skin.

The terms "treatment", "therapeutic use", "cosmetic use" and "medicinal use" shall refer to any and all uses of the disclosed compositions which remedy a disease state, one or more symptoms or one or more effects, or otherwise prevent, hinder, retard, or reverse the progression of disease or one or more other undesirable symptoms or effects in any way whatsoever.

Further provided are methods and pharmaceutical and/or cosmetic compositions for inhibiting skin pigmentation comprising the use of the present compounds either alone or in combination with other, like-acting agents, For example, such additional agents may include agents that are believed to function by mimicking or increasing P-protein function, and/or by modifying late endosomal/lysosomal trafficking. Such pharmaceutical compositions and their corresponding methods are useful for decreasing and/or inhibiting melanin production and, therefore, for reducing skin pigmentation. These agents may be used singly, in combination with one another, or in combination with other drugs that inhibit pigmentation. By way of a non-limiting example, other drugs that inhibit pigmentation include agents such as tyrosinase inhibitors. Preferably, the methods and compositions disclosed herein are for application to a vertebrate, more particularly to a mammal, and most preferably to a human.

The term "about" is used herein to mean approximately, roughly, around, or in the region of. When the term "about" is used in conjunction with a numerical range, it modifies that range by extending the boundaries above and below the numerical values set forth.

By the phrase "decrease in melanin production" or "inhibiting melanogenesis" is meant a detectable lowering of the amount of melanin synthesized de novo by a melanocyte exposed to a compound disclosed herein, as compared with the amount of melanin synthesized de novo by a control, untreated melanocyte. The term "lowering" as presently used refers, in a first instance, to a decrease of at least about 10%, in a further instance, to a decrease of at least about 25%, and in a still further instance, to a decrease of at least about 50%, in the amount of melanin synthesized de novo.

As one skilled in the art would know in view of this disclosure, the compounds used in the methods disclosed herein may be used alone or in combination with each other. Moreover, the methods also include the additional use of other compounds known in the art to affect melanin synthesis such as tyrosinase inhibitors. Such inhibitors are known to those skilled in the art and include various derivatives of resorcinol, hydroquinone, kojic acid, melamine, and various types of plant extracts, among others.

Thus, the disclosure relates both to methods of modifying, and particularly inhibiting the pigmentation of skin in which the active compound used, or a pharmaceutically acceptable salt thereof, and one or more of the other active ingredients referred to above are administered together, as part of the same pharmaceutical composition, as well as methods in which they are administered separately as part of an appropriate dose regimen designed to obtain the benefits of the combination therapy. The appropriate dose regimen, the amount of each dose administered, and specific intervals between doses of each active agent will depend upon the specific combination of active agents employed, the condition of the patient being treated, and the nature and severity of the disorder or condition being treated. Such additional active ingredients will generally be administered in amounts less than or equal to those for which they are effective as single topical therapeutic agents. The FDA approved dosages for such active agents that have received FDA approval for administration to humans are publicly available.

For example, any of the compounds used according to a skin-lightening method disclosed herein may be used in combination with a tyrosinase inhibitor or other skin-whitening agent as currently known in the art or to be developed in the future, including any one or more of those agents described in the following patent publications: U.S. Pat. No. 4,278,656 to Nagai et al, issued Jul. 14, 1981; U.S. Pat. No. 4,369,174 to Nagai et al., issued Jan. 18, 1983; U.S. Pat. No. 4,959,393 to Torihara et al., issued Sep. 25, 1990; U.S. Pat. No. 5,580,549 to Fukuda et al., issued Dec. 3, 1996; U.S. Pat. No. 6,123,959 to Jones et al., issued Sep. 26, 2000; U.S. Pat. No. 6,132,740 to Hu, issued Oct. 17, 2000; U.S. Pat. No. 6,159,482 to Tuloup et al., issued Dec. 12, 2000; WO 99/32077 by L'Oreal, published Jul. 1, 1999; WO 99/64025 by Fytokem Prod. Inc., published Dec. 16, 1999; WO 00/56702 by Pfizer Inc., published Sep. 28, 2000; WO 00/76473 by Shiseido Co. Ltd., published Dec. 12, 2000; EP 997140 by L'Oreal S A, published May 3, 2000; JP 5221846 by Kunimasa Tomoji, published Aug. 31, 1993; JP 7242687 by Shiseido Co. Ltd., published Sep. 19, 1995; JP 7324023 by Itogawa H, published Dec. 12, 1995; JP 8012552 by Shiseido Co. Ltd., published Jan. 16, 1996; JP 8012554 by Shiseido Co. Ltd., published Jan. 16, 1996; JP 8012557 by Shiseido Co. Ltd., published Jan. 16, 1996; JP 8012560 by Shiseido Co. Ltd., published Jan. 16, 1996; JP 8012561 by Shiseido Co. Ltd., published Jan. 16, 1996; JP 8134090 by Fujisawa, published May 28, 1996; JP 8168378 by Kirinjo KK, published Jul. 2, 1996; JP 8277225 by Kansai Koso KK, published Oct. 22, 1996; JP 9002967 by Sanki Shoji KK, published Jan. 7, 1997; JP 9295927 by Yagi Akira, published Nov. 18, 1997; JP 10072330 by Kansai Kouso, published Mar. 17, 1998; JP 10081626 by Kamiyama KK, published Mar. 31, 1998; JP 10101543 by Kansai Kouso KK, published Apr. 21, 1998; JP 11071231 by Maruzen Pharm., published Mar. 16, 1999; JP 11079934 by Kyodo Nyugyo, published Mar. 23, 1999; JP 11246347 by Shiseido Co. Ltd., published Sep. 14, 1999; JP 11246344 by Shiseido Co. Ltd., published Sep. 14, 1999; JP 2000-080023 by Kanebo Ltd., published Mar. 21, 2000; JP 2000-095663 by Kose KK, published Apr. 4, 2000; JP 2000-159681 by Hai Tai Confectionary Co. Ltd., published Jun. 13, 2000; JP 2000-247907 by Kanebo Ltd., published Sep. 12, 2000; JP-9002967 by Sanki Shoji KK, published Jan. 7, 1997; JP-7206753 by Nikken Food KK, published Aug. 8, 1995; JP-5320025 by Kunimasa T, published Dec. 3, 1993; and JP-59157009 by Yakurigaku Chuou KE, published Sep. 6, 1984; among others; all of which patent publications are incorporated herein by reference.

In another aspect, provided are methods of reducing skin pigmentation. In this method the skin is contacted with a pharmaceutically effective amount of a compound of the invention, that results in a reduction of skin pigmentation.

By the phrase "reducing skin pigmentation" is meant a detectable decrease in the amount of melanin in the skin, preferably causing a lightening of the skin as a result of a lowering of the amount of melanin synthesized de novo. The term "lowering" as presently used refers, in a first instance, to a decrease of at least about 10%, in a further instance, to a decrease of at least about 25%, and in a still further instance, to a decrease of at least about 50%, in the amount of melanin synthesized de novo. This lowering of melanin synthesized de novo is preferably visually distinguishable to the naked eye, i.e., would not require the aid of a microscope or other such means to detect its occurrence.

Also provided are methods for a reduction in skin pigmentation by contacting the skin topically with an effective amount of a compound that alters late endosomal/lysosomal trafficking in the skin. Useful compounds for these methods include those disclosed above.

Pharmaceutical Applications

For pharmaceutical uses, it is preferred that the compounds disclosed herein are part of a pharmaceutical composition. Pharmaceutical compositions, comprising an effective amount of such a compound in a pharmaceutically acceptable carrier, can be administered to a patient, person, or animal having a disease, disorder, or condition which is of a type that produces, or overproduces, melanin.

The amount of compound which will be effective in the treatment of a particular disease, disorder, or condition will depend on the nature of the disease, disorder, or condition, and can be determined by standard clinical techniques. Where possible, it is desirable to determine in vitro the cytotoxicity of the compound to the tissue type to be treated, and then in a useful animal model system prior to testing and use in humans.

The compound can be administered for the reduction or increase of melanin synthesis by any means that results in contact of the active agent with its site of action in the body of a mammal. The compounds can be administered by any conventional means available for use in conjunction with pharmaceuticals, either as individual therapeutic agents or in a combination of therapeutic agents. Each can be administered alone, but is preferably administered with a pharmaceutical carrier selected on the basis of the chosen route of administration and standard pharmaceutical practice. The pharmaceutical compositions can be adapted for oral, parenteral, rectal, and preferably topical, administration, and can be in unit dosage form, in a manner well known to those skilled in the pharmaceutical art. Parenteral administration includes but is not limited to, injection subcutaneously, intravenously, intraperitoneally or intramuscularly. However, topical application is preferred.

Cosmetic Applications

In addition to pharmaceutical uses, the methods disclosed herein are useful for cosmetic purposes. Cosmetic applications for methods disclosed herein include the topical application of compositions containing one or more compounds to enhance or otherwise alter the visual appearance of skin or hair. Occurrences in the skin or hair of noticeable but undesired pigmentation as a result of melanin production or overproduction can be treated using the methods disclosed herein. Thus, and as discussed above, the compounds and compositions can be used to achieve improvements in skin or hair appearance, as by brightening the same, adding or enhancing luster, and the like. Suitable formulations for these purposes can be prepared by those skilled in the art, and such details of preparation are considered within the scope.

The phrases "pharmaceutical applications" and "cosmetic applications" are not meant to imply mutual exclusiveness. In some embodiments, a composition may be applied to both a "pharmaceutical application" and a "cosmetic application" dependent upon the need and course of action called for.

Endpoints and Dosages

An effective dosage and treatment protocol can be determined by conventional means, starting with a low dose in laboratory animals and then increasing the dosage while monitoring the effects, and systematically varying the dosage regimen as well. Animal studies, preferably mammalian studies, are commonly used to determine the maximal tolerable dose, or MTD, of a bioactive agent per kilogram weight. Those skilled in the art can extrapolate doses for efficacy and avoidance of toxicity to other species, including humans.

Before human studies of efficacy are undertaken, Phase I clinical studies in normal subjects can help establish safe doses. Numerous factors can be taken into consideration by a clinician when determining an optimal dosage for a given subject. Primary among these is the toxicity and half-life of the chosen compound. Additional factors include the size of the patient, the age of the patient, the general condition of the patient, the particular disease, condition, or disorder being treated, the severity of the disease, condition, or disorder being treated, the presence of other drugs in the patient, the effect desired, and the like. The trial dosages would be chosen after consideration of the results of animal studies and the clinical literature.

One of ordinary skill in the art will appreciate that the endpoint chosen in a particular case will vary according to the disease, condition, or disorder being treated, the outcome desired by the patient, subject, or treating physician, and other factors. Where the composition is being used for cosmetic purposes, such as to lighten skin color such as, for example, to reverse hyperpigmentation caused by, for example, inflammation or diseases such as melasma, or to modify hair color, any one of a number of endpoints can be chosen.

In such instance, endpoints can be defined subjectively such as, for example, when the subject is simply "satisfied" with the results of the treatment. For pharmacological applications, the endpoint can be determined by the patient's, or the treating physicians, satisfaction with the results of the treatment. Alternatively, endpoints can be defined objectively. For example, the patient's or subject's skin or hair in the treated area can be compared to a color chart. Treatment is terminated when the color of the skin or hair in the treated area is similar in appearance to a color on the chart. Alternatively, the reflectance of the treated skin or hair can be measured, and treatment can be terminated when the treated skin or hair attains a specified reflectance. Alternatively, the melanin content of the treated hair or skin can be measured. Treatment can be terminated when the melanin content of the treated hair or skin reaches a specified value. Melanin content can be determined in any way known to the art, including by histological methods, with or without enhancement by stains for melanin.

Methods of Administration

The disclosed compounds can be administered topically, e.g., as patches, ointments, creams, gels, lotions, sera, solutions, foams, masks or transdermal administration. The compounds can also be administered orally in solid or semi-solid dosage forms, such as hard or soft-gelatin capsules, tablets, or powders, or in liquid dosage forms, such as elixirs, syrups, or suspensions. Additionally, the compounds can also be administered parenterally, in sterile liquid dosage forms or in suppository form.

Because in vivo use is contemplated, the composition is preferably of high purity and substantially free of potentially harmful contaminants, e.g., at least National Food (NF) grade, generally at least analytical grade, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

Useful pharmaceutical dosage forms for administration of the present compounds are described below.

The pharmaceutical compositions can be applied directly to the skin. Alternatively, they can be delivered by various transdermal drug delivery systems, such as transdermal patches as known in the art. For example, for topical administration, the active ingredient can be formulated in a solution, gel, lotion, ointment, cream, suspension, foam, mask, paste, liniment, powder, tincture, aerosol, patch, or the like in a pharmaceutically or cosmetically acceptable form by methods well known in the art. The composition can be any of a variety of forms common in the pharmaceutical or cosmetic arts for topical application to animals or humans, including solutions, lotions, sprays, creams, ointments, salves, gels, etc., as described below. Preferred agents are those that are viscous enough to remain on the treated area, those that do not readily evaporate, and/or those that are easily removed by rinsing with water, optionally with the aid of soaps, cleansers and/or shampoos. Actual methods for preparing topical formulations are known or apparent to those skilled in the art, and are described in detail in *Remington's Pharmaceutical Sciences*, 1990 (supra); and *Pharmaceutical Dosage Forms and Drug Delivery Systems*, 6th ed., Williams & Wilkins (1995).

In order to enhance the percutaneous absorption of the active ingredients, one or more of a number of agents can be added in the topical formulations including, but not limited to, dimethylsulfoxide, dimethylacetamide, dimethylformamide, surfactants, azone, alcohol, acetone, propylene glycol and polyethylene glycol. In addition, physical methods can also be used to enhance transdermal penetration such as, e.g., by iontophoresis or sonophoresis. Alternatively, or in addition, liposomes may be employed.

A topically applied composition contains a pharmaceutically effective amount of at least one of the disclosed compounds as described herein, and those ingredients as are necessary for use as a carrier, such as an emulsion, a cream, an ointment, an ophthalmic ointment, an aqueous solution, a lotion or an aerosol. Non-limiting examples of such carriers are described in more detail below and may be found in International Patent Publication WO 00/62742, published Oct. 26, 2000, U.S. Pat. No. 5,691,380 to Mason et al., issued on Nov. 25, 1997 and U.S. Pat. No. 5,968,528 to Deckner et al., issued on Oct. 19, 1999, U.S. Pat. No. 4,139,619 to Chidsey, III, issued on Feb. 13, 1979 and U.S. Pat. No. 4,684,635 to Orentreich et al., issued on Aug. 4, 1987 which are incorporated herein by reference. Suitable pharmaceutical carriers are further described in *Remington's Pharmaceutical Sciences*, 17th ed., Mack Publishing Company, Easton, Pa. (1990) a standard reference text in this field.

The pharmaceutical compositions may also include optional components. Such optional components should be suitable for application to keratinous tissue, that is, when incorporated into the composition, they are suitable for use in contact with human keratinous tissue without undue toxicity, incompatibility, instability, allergic response, and the like within the scope of sound medical judgment. In addition, such optional components are useful provided that they do not unacceptably alter the benefits of the active compounds disclosed herein. The *CTFA Cosmetic Ingredient Handbook*, Second Edition (1992) describes a wide variety of non-limiting cosmetic and pharmaceutical ingredients commonly used in the skin care industry, which are suitable for use in the compositions disclosed herein. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

In addition to the pharmaceutically effective amount of an agent disclosed herein, the topical compositions also comprise a dermatologically acceptable carrier. The phrase "dermatologically acceptable carrier", as used herein, means that the carrier is suitable for topical application to the skin, i.e., keratinous tissue, has good aesthetic properties, is compatible with the active agents disclosed herein and any other components, and will not cause any safety or toxicity concerns. A safe and effective amount of carrier is from about 10% to about 99.99%, preferably from about 30% to about 99.9%, more preferably from about 50% to about 98%, and most preferably from about 60% to about 95% of the composition.

The carrier utilized in the disclosed compositions can be in a wide variety of forms. These include emulsion carriers, including, but not limited to, oil-in-water, water-in-oil, water-in-oil-in-water, and oil-in-water-in-silicone emulsions, a cream, an ointment, an ophthalmic ointment, an aqueous solution, a lotion or an aerosol. As will be understood by the skilled artisan, a given component will distribute primarily into either the water or oil/silicone phase, depending on the water solubility/dispersibility of the component in the composition.

Emulsions generally contain a pharmaceutically effective amount of an agent disclosed herein and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560, issued to Dickert, et al. Aug. 28, 1973; U.S. Pat. No. 4,421,769, issued to Dixon, et al., Dec. 20, 1983; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions as disclosed herein comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain a polyorganosiloxane oil. A preferred water-in-silicone emulsion system is formulated to provide an oxidatively stable vehicle for delivery of a pharmaceutically effective amount of an agent disclosed herein. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compounds disclosed herein in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g. mineral oil, vegetable oils, synthetic oils. semisynthetic oils, etc.

Useful topical compositions comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

Topical compositions typically comprise from about 25% to about 90%, preferably from about 40% to about 80%, more preferably from about 60% to about 80%, water in the dispersed aqueous phase by weight of the composition.

The water-in-silicone emulsions preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in *McCutcheon's Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371 to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions comprise from about 0.5% to about 20%, more preferably from about 1% to about 10%, most preferably from about 1% to about 5%, by weight of the composition, of a structuring agent. The preferred structuring agents are selected from the group consisting of stearic acid, palmitic acid, stearyl alcohol, cetyl alcohol, behenyl alcohol, stearic; acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See, *McCutcheon's. Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al. issued Dec. 20, 1983; and U.S. Pat. No. 3,755,560. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued Sep. 29, 1992; U.S. Pat. No. 5,151,210 to Steuri et al. issued Sep. 29, 1992; U.S. Pat. No. 5,120,532; U.S. Pat. No. 4,387,090; U.S. Pat. No. 3,155,591; U.S. Pat. No. 3,929,678; U.S. Pat. No. 3,959,461; *McCutcheon's, Detergents & Emulsifiers* (North American edition 1979) M.C. Publishing Co.; and Schwartz, et al., *Surface Active Agents, Their chemistry and Technology*, New York: Interscience Publishers, 1949.

Alternatively, other useful cationic emulsifiers include amino-amides. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

A wide variety of anionic surfactants are also useful herein. See, e.g., U.S. Pat. No. 3,929,678, to Laughlin et al., issued Dec. 30, 1975. In addition, amphoteric and zwitterionic surfactants are also useful herein.

The preferred oil-in-water emulsion comprises from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions disclosed herein, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. See, e.g., Sagarin, *Cosmetics, Science and Technology*, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the embodiments disclosed herein generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an agent described herein. A cream typically comprises from about 5% to about 50%, preferably from about 10% to about 20% of emollient; from about 45% to about 85%, preferably from about 50% to about 75% water; and a pharmaceutically effective amount of an agent described herein.

Ointments may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, *Cosmetics, Science and Technology*, 2nd Edition, Vol. 1, pp. 72-73 (1972), incorporated herein by reference, and/or an emollient. For example, an ointment may comprise from about 2% to about 10% of an emollient; from about 0.1% to about 2% of a thickening agent; and a pharmaceutically effective amount of an agent described herein.

By way of non-limiting example, 1000 g of topical cream is prepared from the following types and amounts of ingredients: a pharmaceutically effective amount of an agent disclosed herein, tegacid regular (150 g) (a self-emulsifying glyceryl monostearate from Goldschmidt Chemical Corporation, New York, N.Y.), polysorbate 80 (50 g), spermaceti (100 g), propylene glycol (50 g), methylparaben (1 g), and deionized water in sufficient quantity to reach 1000 gm. The tegacid and spermaceti are melted together at a temperature of 70-80° C. The methylparaben is dissolved in about 500 g of water and the propylene glycol, polysorbate 80, and 6-amino-1,2-dihydro-1-hydroxy-2-imino-4-piperidinopyrimidine free base are added in turn, maintaining a temperature of 75-80° C. The methylparaben mixture is added slowly to the tegacid and spermaceti melt, with constant stirring. The addition is continued for at least 30 minutes with additional stirring until the temperature has dropped to 40-45° C. Finally, sufficient water is added to bring the final weight to 1000 g and the preparation stirred to maintain homogeneity until cooled and congealed.

By way of non-limiting example, 1000 g of a topical ointment is prepared from the following types and amounts of ingredients: a pharmaceutically effective amount of an agent disclosed herein, zinc oxide (50 g), calamine (50 g), liquid petrolatum (heavy) (250 g), wool fat (200 g), and enough white petrolatum to reach 1000 g. Briefly, the white petrolatum and wool fat are melted and 100 g of liquid petrolatum added thereto. The pharmaceutically effective amount of an agent disclosed herein, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

By way of non-limiting example, 1000 g of an ointment, e.g., an ophthalmic ointment, containing a pharmaceutically effective amount of an agent disclosed herein is prepared from the following types and amounts of ingredients: a pharmaceutically effective amount of an agent disclosed herein, light liquid petrolatum (250 g), wool fat (200 g), and enough white petrolatum to reach 1000 g. Briefly, the pharmaceutically effective amount of an agent disclosed herein is finely divided and added to the light liquid petrolatum. The wool fat and white petrolatum are melted together, strained, and the temperature adjusted to 45-50° C. The liquid petrolatum slurry is added, and the ointment stirred until congealed.

By way of non-limiting example, 1000 ml of an aqueous solution containing a pharmaceutically effective amount of an agent disclosed herein is prepared from the following types and amounts of ingredients: a pharmaceutically effective amount of an agent disclosed herein, polyethylene glycol 4000 (120 g) myristyl-gamma-picolinium chloride (0.2 g), polyvinylpyrrolidone (1 g), and enough deionized water to reach 1000 milliliters. Briefly, the ingredients are dissolved in the water and the resulting solution is sterilized by filtration.

By way of non-limiting example, 1000 g of lotion containing a pharmaceutically effective amount of an agent disclosed herein is prepared from the following types and amounts of ingredients: a pharmaceutically effective amount of an agent disclosed herein, N-methyl pyrolidone (40 g), and enough propylene glycol to reach 1000 g.

By way of non-limiting example, an aerosol containing a pharmaceutically effective amount of an agent disclosed herein is prepared from the following types and amounts of materials: a pharmaceutically effective amount of an agent disclosed herein, absolute alcohol (4.37 g), Dichlorodifluoroethane (1.43 g) and dichlorotetrafluoroethane (5.70 g). Briefly, the pharmaceutically effective amount of an agent disclosed herein is dissolved in the absolute alcohol and the resulting solution filtered to remove particles and lint. This solution is chilled to about −30° C. Then, to this is added the chilled mixture of dichlorodifluoromethane and dichlorotetrafluoroethane.

For oral administration, Gelatin capsules or liquid-filled soft gelatin capsules can contain the active ingredient and powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and to protect the tablet from the atmosphere, or enteric-coated for selective, targeted disintegration in the gastrointestinal tract. Liquid dosage forms for oral administration can contain coloring and/or flavoring to increase patient acceptance.

In general, sterile water, oil, saline, aqueous dextrose (glucose), polysorbate and related sugar solutions and glycols such as propylene glycol or polyethylene glycols, are suitable carriers for parenteral solutions. Solutions or emulsions for parenteral administration preferably contain about 5-15% polysorbate 80 or lecithin, suitable stabilizing agents and, if necessary, buffer substances. Antioxidizing agents such as, but not limited to, sodium bisulfite, sodium sulfite, or ascorbic acid, either alone or combined, are suitable stabilizing agents. Also useful are citric acid and its salts, and sodium EDTA. In addition, parenteral solutions can contain preservatives including, but not limited to, benzalkonium chloride, methyl- or propyl-paraben, and chlorobutanol.

As will be understood by those in the art, the compositions and pharmaceutical compositions may be provided in the form of a kit. Kits comprise one or more specific compositions and/or pharmaceutical compositions disclosed herein. Optionally, the kit further contains printed instructions as a label or package insert directing the use of such reagents to modify skin pigmentation, i.e., to lighten skin as appropriate to the particular included composition. These compounds are provided in a container designed to prevent contamination, minimize evaporation or drying of the composition, etc. The compounds may or may not be provided in a preset unit dose or usage amount.

The following formulation examples illustrate representative pharmaceutical compositions that may be prepared in accordance with the embodiments disclosed herein, but are not meant to be limited to the following pharmaceutical compositions.

Formulation 1

Tablets

An effective amount of a compound as in Formulae I-VIIb may be admixed as a dry powder with a dry gelatin binder in an approximate 1:2 weight ratio. A minor amount of magnesium stearate may be added as a lubricant. The mixture may then be formed into 240-270 mg tablets (80-90 mg of active compound per tablet) in a tablet press.

Formulation 2

Capsules

An effective amount of a compound as in Formulae I-VIIb may be admixed as a dry powder with a starch diluent in an approximate 1:1 weight ratio. The mixture may then be filled into 250 mg capsules (125 mg of active compound per capsule).

Formulation 3

Liquid

An effective amount of a compound as in Formulae I-VIIb (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4

Tablets

An effective amount of a compound as in Formulae I-VIIb may be admixed as a dry powder with a dry gelatin binder in an approximate 1:2 weight ratio. A minor amount of magnesium stearate may then be added as a lubricant. The mixture may then be formed into 450-900 mg tablets (150-300 mg of active compound) in a tablet press.

Formulation 5

Injection

An effective amount of a compound as in Formulae I-VIIb may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of a compound as in Formulae I-VIIb (10-50 g of active compound) methylparaben (0.25 g), propylparaben (0.15 g), sodium lauryl sulfate (10 g), and propylene glycol (120 g) dissolved in water (about 370 g) may then be added and the resulting mixture is stirred until it congeals.

General Synthetic Procedures

The coumarin compounds as in Formulae I-VIIb which comprise various known drugs or drug like molecules can be purchased from commercial sources and tested for their activities. The coumarin compounds which are not commercially available can be prepared from readily available starting materials using various general methods and procedures known in the art.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

EXAMPLES

Example 1

Screening of Compounds in Cultured Murine Melanocytes

The Spectrum Collection library consisting of 2000 drug compounds or natural products represents a source for the identification of compounds useful in the present invention. The library may be screened to identify novel pigmentation inhibitors in cultured murine melanocytes (melan-a). Compounds are dissolved in dimethylsulfoxide (DMSO) to a final concentration of 10 mM. Screening is performed with cultured melanocytes in 24-well plates followed by melanin assay (see below). A minimum change of 50% in melanin formation is established as significant for a pigmentation inhibitor. DMSO may be used as a negative control and the widely used depigmenting agent, hydroquinone, may be used as a positive control on every plate. Primary screening is performed at a final concentration of 1 μM and potential candidates from the primary screening are reconfirmed in duplicate at final concentrations of 1 and 5 μM.

Melan-a cells are plated at $5 \times 10^4$ cells per well in 1 ml of culture media in 24-well plates the day before adding the library compounds. All compounds are added at the indicated final concentrations. Cells are harvested after 72 hours of incubation, and the melanin assay is performed.

For further test and mechanism of action studies, the compounds may be purchased from Sigma, MicroSource or other known suppliers. The compounds are dissolved in dimethylsulfoxide (DMSO) to a final concentration of 10 mM, and are tested for their effect on melanin synthesis at the indicated final concentrations.

Example 2

Melanin Assay

For the primary and secondary screening, cells were harvested and dissolved in 200 μl of 2N NaOH in 20% DMSO at 70° C. A 180-μl aliquot of the resulting solution was measured for absorbance at 490 nm.

Cells are harvested in extraction buffer (1% Triton X-100, 50 mM Tris, 2 mM EDTA, 150 mM NaCl, pH 7.5) containing a complete protease inhibitor cocktail (Roche). The lysates were centrifuged at 14,000 rpm for 10 minutes at 4° C. BCA protein assay kit (Pierce) was used to measure the protein concentrations of the supernatants, and bovine serum albumin was used as a standard. The remaining pellets were incubated with 100 μl ethanol-ether (1:1) for 10 minutes at room temperature. After removing the ethanol-ether, the pellets were dissolved in 200 μl of 2N NaOH in 20% DMSO at 70° C. A 180-μl aliquot of the resulting solution was measured for absorbance at 490 nm. The melanin contents were normalized to the total amount of protein.

The compounds, their structures, inhibition data expressed as % of control remaining, and available $IC_{50}$ data are shown in Table 1, below.

TABLE 1

Activity Data for Compounds Useful as Melanogenesis Modifiers

| ID | Name | Structure | % of control melanin remaining after treatment @ 1 μM | % of control melanin remaining after treatment @ 5 μM |
|---|---|---|---|---|
| 1 | PRENYLETIN | (structure) | 79 | 80 |

TABLE 1-continued

Activity Data for Compounds Useful as Melanogenesis Modifiers

| ID | Name | Structure | % of control melanin remaining after treatment @ 1 µM | % of control melanin remaining after treatment @ 5 µM |
|---|---|---|---|---|
| 2 | OBLIQUIN | 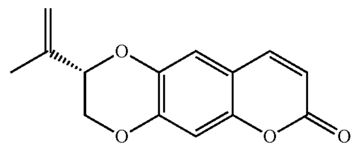 [SMILES: C=C(C)[C@H]1COc2cc3oc(=O)ccc3cc2O1] | 84 | 95 |
| 3 | DIHYDRO-OBLIQUIN | 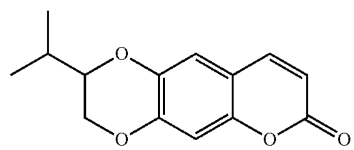 [SMILES: CC(C)C1COc2cc3oc(=O)ccc3cc2O1] | 81 | 81 |
| 4 | FRAXIDIN METHYL ETHER | 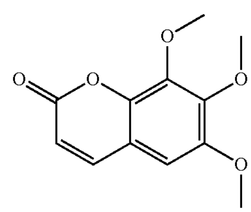 [SMILES: COc1cc2ccc(=O)oc2c(OC)c1OC] | 87 | 95 |
| 5 | XANTHYLETIN | 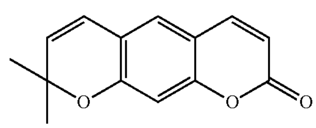 [SMILES: CC1(C)C=Cc2cc3ccc(=O)oc3cc2O1] | 99 | 110 |
| 6 | IMPERATORIN | 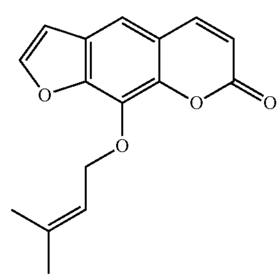 [SMILES: CC(C)=CCOc1c2occc2cc2ccc(=O)oc12] | 91 | 96 |
| 7 | PACHYRRHIZIN | 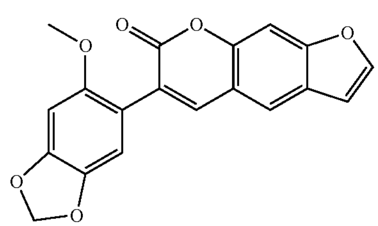 [SMILES: COc1cc2c(cc1-c1cc3cc4ccoc4cc3oc1=O)OCO2] | 75 | 71 |
| 8 | HERNIARIN | 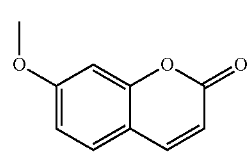 | 84 | 81 |

TABLE 1-continued

Activity Data for Compounds Useful as Melanogenesis Modifiers

| ID | Name | Structure | % of control melanin remaining after treatment @ 1 μM | % of control melanin remaining after treatment @ 5 μM |
|---|---|---|---|---|
| 9 | ROBUSTIC ACID METHYL ETHER | 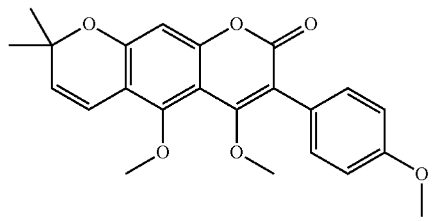 | 69 | 16 |
| 10 | ROBUSTIC ACID | 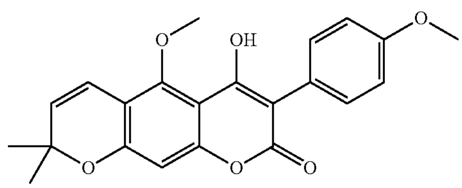 | 91 | 93 |
| 11 | KUHLMANNIN | 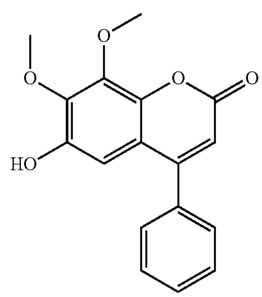 [SMILES: COc1c(O)cc2c(-c3ccccc3)cc(=O)oc2c1OC] | 81 | 84 |
| 12 | SPHONDIN | 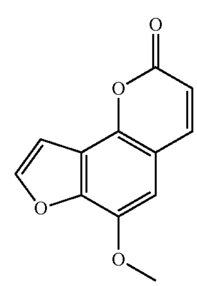 [SMILES: COc1cc2ccc(=O)oc2c2ccoc12] | 89 | 101 |
| 13 | ISOPIMPINELLIN | 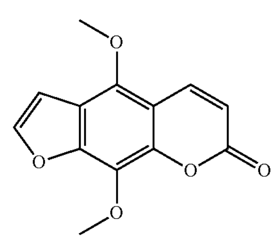 [SMILES: COc1c2ccoc2c(OC)c2oc(=O)ccc12] | 86 | 95 |

TABLE 1-continued

Activity Data for Compounds Useful as Melanogenesis Modifiers

| ID | Name | Structure | % of control melanin remaining after treatment @ 1 μM | % of control melanin remaining after treatment @ 5 μM |
|---|---|---|---|---|
| 14 | PIMPINELLIN | 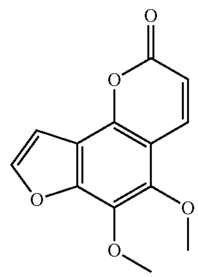 [SMILES: COc1c(OC)c2occc2c2oc(=O)ccc12] | 76 | 109 |
| 15 | ISOBERGAPTENE | 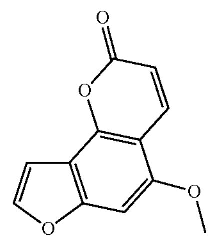 [SMILES: COc1cc2occc2c2oc(=O)ccc12] | 86 | 108 |
| 16 | SCANDENIN | 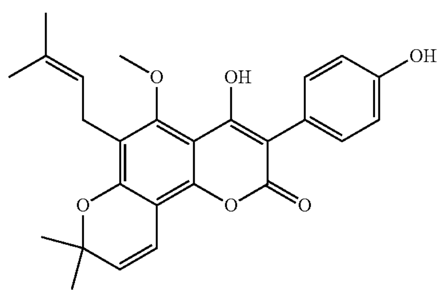 [SMILES: COc1c(CC=C(C)C)c2c(c3oc(=O)c(-c4ccc(O)cc4)c(O)c13)C=CC(C)(C)O2] | 90 | 64 |
| 17 | HYMECROMONE METHYL ETHER | 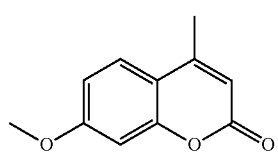 | 96 | 93 |
| 18 | BERGAPTENE | 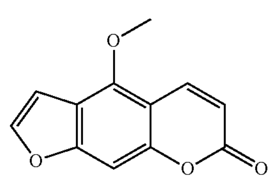 [SMILES: COc1c2ccoc2cc2oc(=O)ccc12] | 100 | 93 |
| 19 | COUMOPHOS | 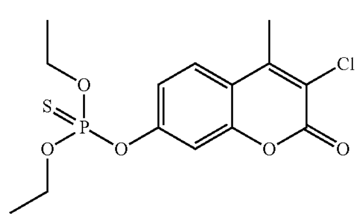 [SMILES: CCOP(=S)(OCC)Oc1ccc2c(C)c(Cl)c(=O)oc2c1] | 81 | 48 |

TABLE 1-continued

Activity Data for Compounds Useful as Melanogenesis Modifiers

| ID | Name | Structure | % of control melanin remaining after treatment @ 1 μM | % of control melanin remaining after treatment @ 5 μM |
|---|---|---|---|---|
| 20 | METHOXSALEN | 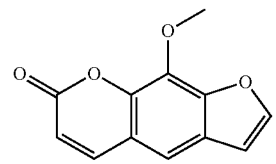 [SMILES: COc1c2occc2cc2ccc(=O)oc12] | 120 | 125 |
| 21 | NOVOBIOCIN SODIUM | 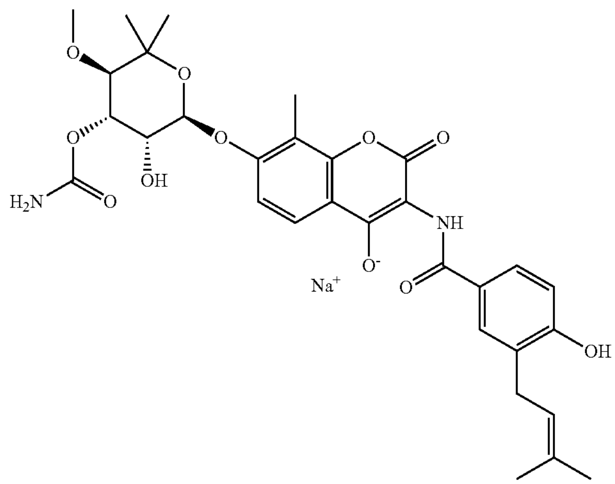 [SMILES: CO[C@@H]1[C@@H](OC(N)=O)[C@@H](O)[C@H](Oc2ccc3c([O-])c(NC(=O)c4ccc(O)c(CC=C(C)C)c4)c(=O)oc3c2C)OC1(C)C ; [Na+]] | 90 | 94 |
| 22 | TRIOXSALEN | 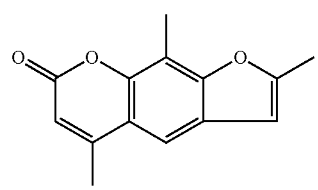 [SMILES: Cc1cc2cc3c(C)cc(=O)oc3c(C)c2o1] | 90 | 118 |
| 23 | CITROPTEN | 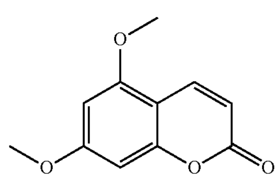 | 86 | 97 |
| 24 | 4-METHYLESCULETIN | 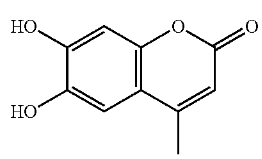 | 88 | 100 |
| 25 | ESCULETIN | 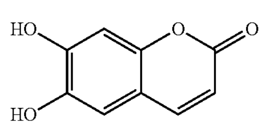 | 87 | 88 |

TABLE 1-continued
Activity Data for Compounds Useful as Melanogenesis Modifiers
| ID | Name | Structure | % of control melanin remaining after treatment @ 1 µM | % of control melanin remaining after treatment @ 5 µM |
|---|---|---|---|---|
| 26 | AESCULIN | 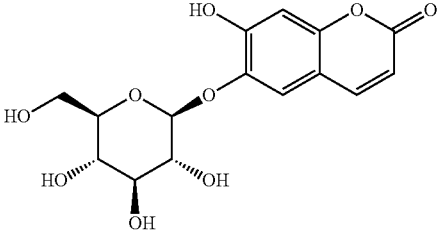 [SMILES: O=c1ccc2cc(O[C@@H]3O[C@H](CO)[C@@H](O)[C@H](O)[C@H]3O)c(O)cc2o1] | 70 | 84 |
| 27 | LOMATIN | 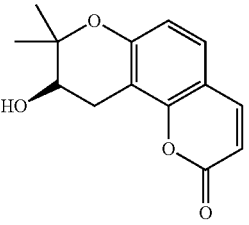 | 89 | 85 |
| 28 | SELINIDIN | 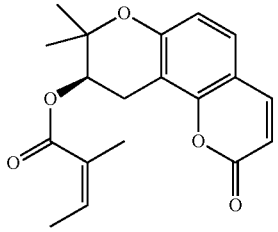 [SMILES: C/C=C(/C)C(=O)O[C@@H]1Cc2c(ccc3ccc(=O)oc23)OC1(C)C] | 85 | 82 |
| 29 | PTERYXIN | 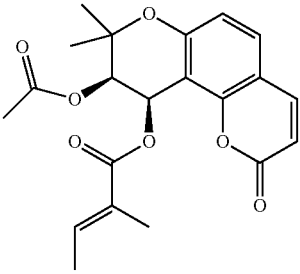 [SMILES: C/C=C(\C)C(=O)O[C@@H]1c2c(ccc3ccc(=O)oc23)OC(C)(C)[C@@H]1OC(C)=O] | 93 | 101 |
| 30 | DIHYDROSAMIDIN | 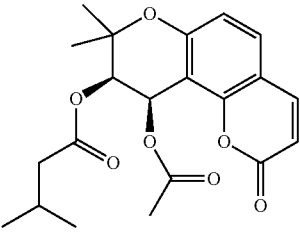 [SMILES: CC(=O)O[C@@H]1c2c(ccc3ccc(=O)oc23)OC(C)(C)[C@@H]1OC(=O)CC(C)C] | 106 | 88 |
| 31 | MARMESIN | 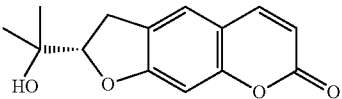 [SMILES: CC(C)(O)[C@@H]1Cc2cc3ccc(=O)oc3cc2O1] | 89 | 97 |

TABLE 1-continued

Activity Data for Compounds Useful as Melanogenesis Modifiers

| ID | Name | Structure | % of control melanin remaining after treatment @ 1 μM | % of control melanin remaining after treatment @ 5 μM |
|---|---|---|---|---|
| 32 | MARMESIN ACETATE | 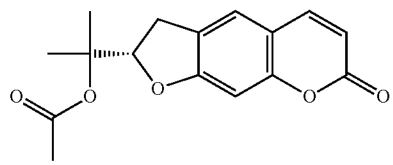 [SMILES: CC(=O)OC(C)(C)[C@@H]1Cc2cc3ccc(=O)oc3cc2O1] | 77 | 92 |
| 34 | PEUCEDANIN | 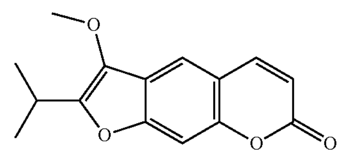 [SMILES: COc1c(C(C)C)oc2cc3oc(=O)ccc3cc12] | 83 | 84 |
| 35 | LONCHOCARPIC ACID | 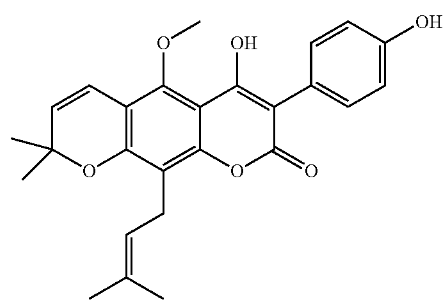 [SMILES: COc1c2c(c(CC=C(C)C)c3oc(=O)c(-c4ccc(O)cc4)c(O)c13)OC(C)(C)C=C2] | 84 | 81 |
| 36 | DERRUSNIN | 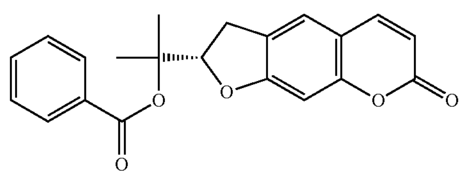 [SMILES: CC(C)(OC(=O)c1ccccc1)[C@@H]1Cc2cc3ccc(=O)oc3cc2O1] | 81 | 87 |
| 37 | 4-METHYLDAPHNETIN | 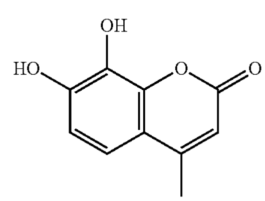 | 83 | 88 |
| 38 | SCOPOLETIN | 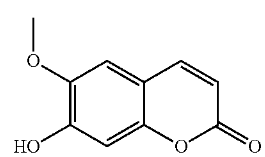 | 77 | 83 |
| 39 | FRAXETIN | 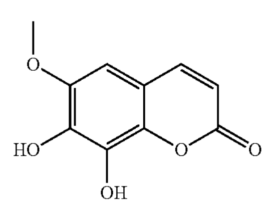 | 84 | 89 |

TABLE 1-continued

Activity Data for Compounds Useful as Melanogenesis Modifiers

| ID | Name | Structure | % of control melanin remaining after treatment @ 1 µM | % of control melanin remaining after treatment @ 5 µM |
|---|---|---|---|---|
| 40 | FELAMIDIN | 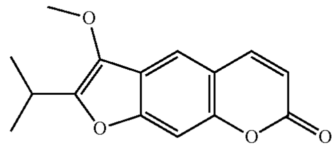 [SMILES: COc1c(C(C)C)oc2cc3oc(=O)ccc3cc12] | 97 | 88 |

Example 3

MelanoDerm™ Pigmentation Assay

The compounds of the invention may be tested in the MelanoDerm™ pigmentation assay, to confirm and demonstrate their activity as inhibitors in a setting that replicates in vivo conditions. MelanoDerm™, made by MatTek Corp., is a viable reconstituted three-dimensional human skin equivalent containing normal melanocytes and keratinocytes that are derived from African-American (MEL-B), Asian (MEL-A) or Caucasian (MEL-C) donors. Both MEL-A and MEL-B tissues are used in the study, and they are maintained in the NMM-113 medium as recommended by the manufacturer.

The test compound is dissolved in 30% ethanol:70% propylene glycol to a final concentration of 1.0 mM (equal to 356.6 µg/ml), and this is maintained constant and used on all samples tested. A 25 µl of its aliquot is applied topically to the MelanoDerm™ tissue (MEL-B) on Days 0, 1, 3, 6, 8 and 10. The MelanoDerm™ tissues are fed every other day with 5 ml fresh NMM-113. Prior to each application, the tissues are washed with 1 ml PBS to remove any residual test compound. Tissues are fixed on Days 10 and 13 for microscopic analysis and histological evaluation. In addition, duplicate tissues are frozen on Days 10 and 13 for the melanin assay.

Similar experiments may be performed on Asian skin equivalent (MEL-A) except: the treatments are applied on Days 0, 1, 3, 6, 8, 10 and 13. Tissues are taken out on Days 13 and 16 for the various assays. 30% ethanol:70% propylene glycol is used as a negative control and the well-known pigmentation inhibitor, arbutin (at concentration of 3 mg/ml), may be used as a positive control.

The experiments are repeated twice on both MEL-A and MEL-B tissues from different lots to make sure that the results are reproducible (study 1 or 2). For each experiment, six tissues are treated with a compound or extract of the invention, and six were treated with vesicle (30% ethanol: 70% PEG) or arbutin if applicable. For MEL-B, on day 10, three tissues under each treatment condition are taken out, and one was used for histological studies and the other two are used for the melanin assay. The same protocol is followed with the MEL-B samples after 13 days' treatment and MEL-A after either 13 or 16 days' treatments.

For the histological studies:
Procedure 1: the effects of the inventive compounds or extract on melanin synthesis in MEL-A or B are evaluated by light microscopy (views from the top surface of the tissue).
Procedure 2: the distribution of melanin in the treated-MEL-A or B is accessed by image analysis using Fontana-Masson stained histological sections (views from the side of the tissue).

For the melanin tissues, the melanin content of each individual tissue is determined, and the final data show the average melanin content of 2 tissues treated under identical conditions.

Those compounds which are found to reduce pigmentation (melanogenesis modifiers or inhibitors; see Table 1) and compositions thereof can be used as topical agents for hair, fur, and/or feather lightening as required. A melanogenesis inhibitor of the invention or a composition thereof may be applied to sites of hyperpigmentation including, without limitation, age spots, freckles, and chloasma. For some individuals, body lightening or whitening of larger skin zones is a cosmetic objective that can be achieved with a more generalized application of a melanogenesis inhibitor of the invention or a composition thereof.

Example 4

Figure 5:
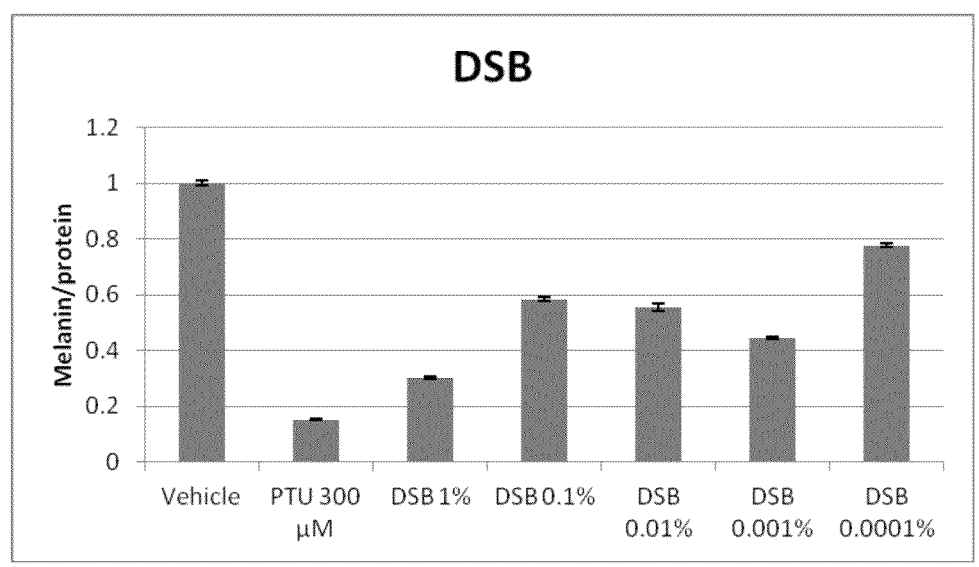
FIG. 5 is a graph of individual dose response testing of the *Derris scandens* benth (DSB) extract of the invention.

Extract Derived from Derris Scandens is a Potent Inhibitor of Melanin Synthesis in Cultured Melanocytes Melan-a cells were plated at $5 \times 10^4$ cells per well in 1 ml of culture media in 24-well plates the day before adding an extract made from a powder prepared from Derris scandens. Ethanol (70%) was used as control and the extract derived from Derris scandens was diluted in cell culture media at the indicated concentrations. Cells were harvested after 72 hours of incubation, and a spectrophotometric melanin assay was performed on cell pellets. The melanin contents were normalized to the total amount of protein. Cell viability was determined by using the CellTiter 96 aqueous nonradioactive cell proliferation assay. FIG. 5 shows that extract derived from Derris scandens is a potent inhibitor of melanin synthesis in cultured melan-a cells.

While certain of the preferred embodiments have been described and specifically exemplified above, it is not intended that the invention be limited to such embodiments. Various modifications may be made thereto without departing from the scope and spirit of the present invention, as set forth in the following claims.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

The chemical names of compounds given in this application were generated using various commercially available chemical naming software tools including MDL's ISIS Draw Autonom Software tool, and were not verified. Particularly, in the event of inconsistency, the depicted structure governs.

What is claimed is:

1. A method for inhibiting melanogenesis or a method for promoting skin lightening in a mammal in need thereof, comprising administering to the mammal an effective amount of either lonchocarpic acid or a compound of formula I:

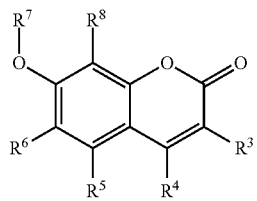

wherein
$R^3$ is selected from the group consisting of halo, substituted or unsubstituted alkyl, substituted or unsubstituted alkenyl, unsubstituted phenyl, 3,4-dihydroxyphenyl, 4-methoxyphenyl, 3,4-dimethoxyphenyl, and substituted or unsubstituted heteroaryl;
$R^4$ is selected from the group consisting of H, halo, hydroxy, alkoxy, alkenyloxy, substituted or unsubstituted alkyl, substituted or unsubstituted alkenyl, and substituted or unsubstituted phenyl;
each $R^5$, $R^6$, and $R^8$ is independently selected from the group consisting of H, halo, hydroxy, alkoxy, alkenyloxy, substituted or unsubstituted alkyl, substituted or unsubstituted alkenyl, and substituted or unsubstituted phenyl;
$R^7$ is selected from the group consisting of H, halo, hydroxy, alkoxy, alkenyloxy, substituted or unsubstituted alkyl, substituted or unsubstituted alkenyl, and heterocycloalkyl; or $R^7$ is —P(=O)(alkoxy)$_2$, or —P(=S)(alkoxy)$_2$; or $R^6$ and $R^7$ or $R^7$ and $R^8$ are joined to form a 5- or 6-membered heterocycloalkyl or heterocycloalkenyl; and the heterocycloalkyl or heterocycloalkenyl is unsubstituted or substituted with one or more groups selected from the group consisting of alkyl, alkenyl, hydroxyalkyl, acyloxyalkyl, hydroxy, and alkoxy; and
provided that the compound is other than robustic acid; or pharmaceutically acceptable salts, solvates, isomers, tautomers, metabolites, analogs, isotopic variants or prodrugs thereof.

2. The method of claim 1 wherein the compound is of formula I; and $R^7$ is selected from the group consisting of H, substituted or unsubstituted alkyl, and substituted or unsubstituted alkenyl.

3. The method of claim 1, wherein the compound is of formula I; and $R^3$ is Cl, alkyl, unsubstituted phenyl, 3,4-dihydroxyphenyl, 4-methoxyphenyl, or 3,4-dimethoxyphenyl.

4. The method of claim 1, wherein the compound is of formula I; and $R^4$ is H, Cl, alkyl, or substituted or unsubstituted phenyl.

5. The method of claim 1, wherein the compound is of formula I; and $R^5$ is H, Cl, alkyl, hydroxy, or alkoxy.

6. The method of claim 1, wherein the compound is of formula I; and $R^6$ is H, Cl, alkyl, alkenyl, hydroxy, alkoxy, or alkenyloxy.

7. The method of claim 1, wherein the compound is of formula I; and $R^8$ is H, Cl, alkyl, alkenyl, hydroxy, alkoxy, or alkenyloxy.

8. The method of claim 1 wherein the compound is of formula I; each $R^4$, $R^5$, $R^6$ is H; $R^7$ is as in claim 1; and $R^8$ is substituted or unsubstituted alkenyl.

9. The method of claim 1, wherein $R^4$ is H, Cl, alkyl, hydroxy, alkoxy, or substituted or unsubstituted phenyl.

10. The method of claim 1, further comprising an additional active agent, and said additional active agent is selected from the group consisting of a pharmacological agent, a skin brightening agent and a skin lightening agent.

11. A method for altering or restoring pigmentation in mammalian skin, hair, wool or fur comprising administering to the mammalian skin, hair, wool or fur an amount of a composition comprising:
a) an amount, which is effective to alter or restore pigmentation in mammalian skin, hair, wool or fur, of one or more compounds of claim 1; and b) a suitable carrier, wherein the amount of the composition is effective to alter or restore pigmentation in mammalian skin, hair, wool or fur.

12. The method of claim 11, wherein the compound is a melanogenesis inhibitor.

13. A method for altering or restoring pigmentation in mammalian hair, wool or fur comprising administering to the mammalian hair, wool or fur an amount, which is effective to alter or restore pigmentation in mammalian hair, wool or fur, of a compound of claim 1 and a cosmetically active agent.

14. The method of claim 13, wherein the cosmetically active agent is a skin lightening compound.

15. The method of claim 1 wherein the compound is of formula IIa, or IIb:

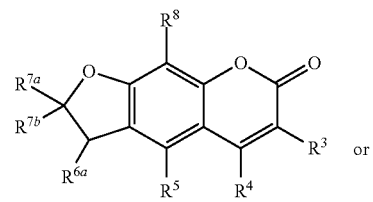

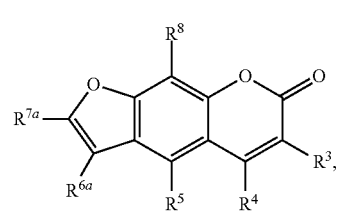

or a pharmaceutically acceptable salt, solvate or prodrug thereof, and stereoisomers, tautomers and isotopic variants thereof; and wherein
$R^3$, $R^4$, $R^5$, and $R^8$ are as in claim 1; and
each $R^{6a}$, $R^{7a}$, and $R^{7b}$ is independently selected from the group consisting of H, alkyl, hydroxyalkyl, and alkenyl.

16. The method of claim 1 wherein the compound is of formula IIIa, or IIIb:

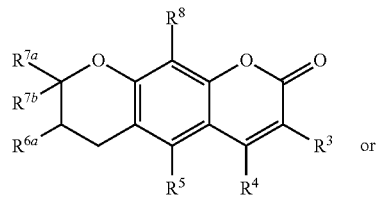

-continued

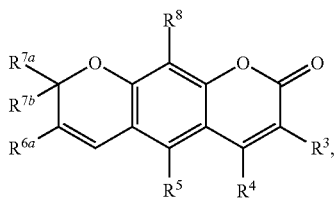
IIIb or a pharmaceutically acceptable salt, solvate or prodrug thereof, and stereoisomers, tautomers and isotopic variants thereof; and wherein $R^3$, $R^4$, $R^5$, and $R^8$ are as in claim 1; and each $R^{6a}$, $R^{7a}$ and $R^{7b}$ is independently selected from the group consisting of H, alkyl, hydroxyalkyl, and alkenyl.

17. The method of claim 1 wherein the compound is of formula IV:

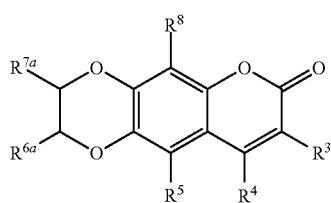
IV or a pharmaceutically acceptable salt, solvate or prodrug thereof, and stereoisomers, tautomers and isotopic variants thereof; and wherein $R^3$, $R^4$, $R^5$, and $R^8$ are as in claim 1; and each $R^{6a}$ and $R^{7a}$ is independently selected from the group consisting of H, alkyl, and alkenyl.

18. The method of claim 1 wherein the compound is of formula Va, or Vb:

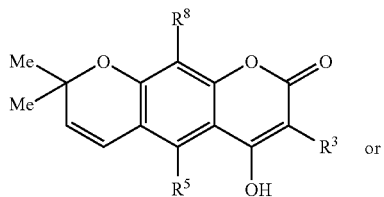
Va

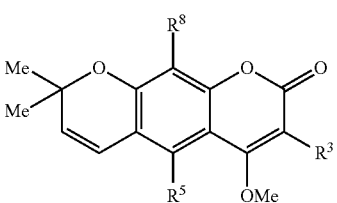
Vb or a pharmaceutically acceptable salt, solvate or prodrug thereof, and stereoisomers, tautomers and isotopic variants thereof; and wherein $R^3$, $R^5$, and $R^8$ are as in claim 1.

19. The method of claim 1 wherein the compound is of formula VIa, or VIb:

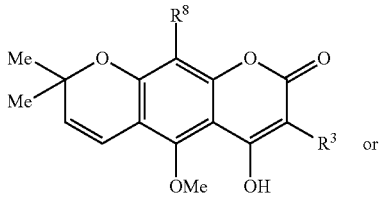
VIa

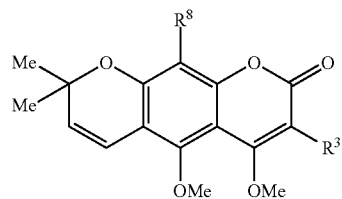
VIb or a pharmaceutically acceptable salt, solvate or prodrug thereof, and stereoisomers, tautomers and isotopic variants thereof; and wherein $R^3$ and $R^8$ are as in claim 1.

20. The method of claim 1 wherein the compound is of formula VIIa:

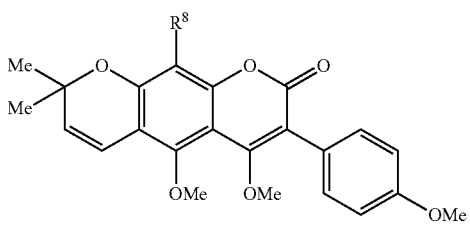
VIIa or a pharmaceutically acceptable salt, solvate or prodrug thereof, and stereoisomers, tautomers and isotopic variants thereof; and wherein $R^8$ is as in claim 1.

21. The method of claim 1, wherein the compound is robustic acid methyl ether.

22. The method of claim 1, wherein the compound is lonchocarpic acid.

* * * * *